(12) United States Patent
Gray et al.

(10) Patent No.: US 12,326,439 B2
(45) Date of Patent: Jun. 10, 2025

(54) DEVICES AND METHODS FOR MAGNETIC DETECTION OF TISSUE MOTION

(71) Applicant: Curi Bio, Inc., Seattle, WA (US)

(72) Inventors: Kevin Gray, Seattle, WA (US); Jason Silver, Seattle, WA (US)

(73) Assignee: Curi Bio, Inc., Seattle, WA (US)

( * ) Notice: Subject to any disclaimer, the term of this patent is extended or adjusted under 35 U.S.C. 154(b) by 0 days.

(21) Appl. No.: 18/547,311

(22) PCT Filed: Feb. 9, 2023

(86) PCT No.: PCT/US2023/062255
§ 371 (c)(1),
(2) Date: Aug. 21, 2023

(87) PCT Pub. No.: WO2023/154775
PCT Pub. Date: Aug. 17, 2023

(65) Prior Publication Data
US 2024/0094186 A1    Mar. 21, 2024

Related U.S. Application Data

(60) Provisional application No. 63/308,474, filed on Feb. 9, 2022.

(51) Int. Cl.
*G01N 33/483* (2006.01)
*C12N 13/00* (2006.01)
*G01N 27/72* (2006.01)

(52) U.S. Cl.
CPC ......... *G01N 33/4833* (2013.01); *C12N 13/00* (2013.01); *G01N 27/72* (2013.01)

(58) Field of Classification Search
None
See application file for complete search history.

(56) References Cited

U.S. PATENT DOCUMENTS 6,263,230 B1 * 7/2001 Haynor ............... A61B 34/20
                                                          600/424
7,413,547 B1    8/2008 Lichtscheidl et al.
(Continued)

FOREIGN PATENT DOCUMENTS

DE   102010052197 A1   5/2012
WO      2017156455 A1   9/2017
(Continued)

OTHER PUBLICATIONS

International Search Report of the International Searching Authority mailed on Jun. 23, 2023, issued in PCT/US23/62255, filed on Feb. 9, 2023, 2 pages.

(Continued)

*Primary Examiner* — Nasima Monsur
(74) *Attorney, Agent, or Firm* — IPkey PLLC

(57) ABSTRACT

Systems, devices, and methods for localizing magnets are useful for biological tissue analysis and other applications. Tissue analysis systems for use with a tissue analysis device may include a storage medium storing computer readable instructions that cause the execution of magnet localization methods. The system may include the tissue analysis device, which includes a magnet and a magnetometer array disposed adjacent to the magnet. When executed by a processor, the instructions cause operations, including recording a magnetic field of the magnet with the magnetometer array, simulating a simulated magnetic field at each magnetometer of the magnetometer array, and estimating positional information of the magnet based upon iterating simulated positional information of the simulated magnet.

18 Claims, 18 Drawing Sheets

(56) References Cited

U.S. PATENT DOCUMENTS

| | | | |
|---|---|---|---|
| 7,561,051 B1* | 7/2009 | Kynor | A61B 5/06 340/572.6 |
| 2004/0059222 A1* | 3/2004 | Nir | A61B 8/0833 600/443 |
| 2006/0200017 A1 | 9/2006 | Monfre et al. | |
| 2006/0217602 A1 | 9/2006 | Abul-Haj et al. | |
| 2008/0026419 A1 | 1/2008 | Bottlang et al. | |
| 2008/0105607 A1 | 5/2008 | Shigesada et al. | |
| 2011/0009608 A1* | 1/2011 | Kim | G01N 35/1074 536/25.41 |
| 2011/0172565 A1 | 7/2011 | Shih et al. | |
| 2013/0029412 A1 | 1/2013 | Reis et al. | |
| 2013/0181323 A9 | 10/2013 | Tran | |
| 2013/0281323 A1 | 10/2013 | Tran | |
| 2015/0112229 A1 | 4/2015 | Ludwin et al. | |
| 2015/0209784 A1* | 7/2015 | Hayden | B03C 1/01 435/287.1 |
| 2017/0260488 A1 | 9/2017 | Costa et al. | |
| 2019/0029549 A1 | 1/2019 | Sniadecki | |
| 2019/0083974 A1 | 3/2019 | Cambron | |
| 2019/0161748 A1* | 5/2019 | Jervis | G01N 33/54326 |
| 2019/0186921 A1 | 6/2019 | Klosinski, Jr. et al. | |
| 2020/0255789 A1 | 8/2020 | Dendorfer | |
| 2020/0305765 A1* | 10/2020 | Herr | A61B 5/4523 |
| 2021/0270922 A1 | 9/2021 | Martens et al. | |
| 2023/0109347 A1 | 4/2023 | Gray et al. | |
| 2023/0265377 A1 | 8/2023 | Sniadecki et al. | |

FOREIGN PATENT DOCUMENTS

| | | | |
|---|---|---|---|
| WO | 2019008505 A1 | 1/2019 | |
| WO | 2019060370 A1 | 3/2019 | |
| WO | 2019106438 A1 | 6/2019 | |
| WO | 2021071954 A1 | 4/2021 | |
| WO | 2021/173887 A1 | 9/2021 | |
| WO | 2022015869 A1 | 1/2022 | |

OTHER PUBLICATIONS

Written Opinion of the International Searching Authority mailed on Jun. 23, 2023, issued in PCT/US23/62255, filed on Feb. 9, 2023, 8 pages.

Hansen, A. et al., "Development of a Drug Screening Platform Based on Engineered Heart Tissue," Circulation Research: New Methods in Cardiovascular Biology; Jul. 9, 2010, pp. 35-44.

Bielawski, Kevin S., et al.; "Real-Time Force and Frequency Analysis of Engineered Human Heart Tissue Derived from Induced Pluripotent Stem Cells Using Magnetic Sensing"; Tissue Engineering: Part C, Methods Article; vol. 22, No. 10; Oct. 1, 2016; 12 pages.

European Communication Pursuant to Rules 161(2) and 162 EPC issued in European Application No. 21761402.3 on Oct. 5, 2022, 3 pages.

Extended European Search Report mailed on Sep. 13, 2023 issued in corresponding European Patent Application No. 20873909.4, filed on Oct. 7, 2020, 11 pages.

International Search Report mailed on Jan. 8, 2021 issued in corresponding International Patent Application No. PCT/US2020/054587, filed on Oct. 7, 2020, 2 pages.

International Search Report mailed on Jun. 29, 2021 for International Application No. PCT/US2021/019748, filed Feb. 25, 2021, 4 pages.

Japanese Notice of Reasons for Refusal mailed on Feb. 19, 2024, issued in the corresponding Japanese App. No. 2022-551564 filed on Aug. 24, 2022, and its English translation thereof; 10 pages.

Supplementary European Search Report mailed on Mar. 1, 2024, issued in the corresponding European App. No. 21761402.3 filed on Aug. 11, 2022; 7 pages.

Written Opinion of the International Searching Authority mailed on Jan. 8, 2021 issued in corresponding International Patent Application No. PCT/US2020/054587, filed on Oct. 7, 2020, 3 pages.

Written Opinion of the International Searching Authority mailed on Jun. 29, 2021 for International Application No. PCT/US2021/019748, filed Feb. 25, 2021, 7 pages.

* cited by examiner

FIG. 8

DEVICES AND METHODS FOR MAGNETIC DETECTION OF TISSUE MOTION

CROSS-REFERENCE TO RELATED APPLICATIONS

This application is a U.S. National Phase of International Patent Application No. PCT/US23/62255, filed on Feb. 9, 2023, which claims the benefit of U.S. Provisional Patent Application No. 63/308,474, filed Feb. 9, 2022, the entireties of which are hereby incorporated by reference.

TECHNICAL FIELD

The present disclosure relates to devices and methods for detecting motional, structural, or volumetric changes of biological tissues.

BACKGROUND

Measurements of movement of biological tissues cultured in vitro can be useful indicators of the health and functionality of said tissues. Such tissues may move spontaneously or may be moved by electrical stimuli or by other means.

US20190029549A1 discloses approaches whereby tissue movement is detected with the use of a magnet embedded in a scaffold encompassed by a tissue. Changes in a magnetic field at a single magnetic field sensor adjacent to the magnet can, in theory, be correlated to the movement of the magnet by the tissue. This can allow for measurement of tissue movements with greater throughput and sensitivity than be achieved using conventional methods such as optical microscopy.

However, there are shortcomings associated with known devices and methods, which are premised on the assumptions that a magnet is positioned in a specific initial location, oriented in a particular direction, and moves effectively in the one-dimensional path in alignment with the particular direction of orientation of the magnet such that the positions of each moving magnet in a set of multiple magnets can be determined by multiplying the magnetic field values from any underlying magnetic sensor by a single numerical constant.

However, the relationship between the measured magnetic field and the magnet position can become non-linear if the magnet moves too far from the sensor due to the highly non-linearly varying distribution of magnetic fields around conventional permanent magnets. Such non-linearity can cause further inaccuracies because it cannot be assumed that the changes in the magnetic field recorded by the magnetic sensor as the magnet moves are linearly correlated to the physical movement of the magnet.

WO2021071954A1 attempts to address this issue by utilizing an empirically derived nonlinear relationship instead of a constant for converting magnetic field readings to changes in magnet position. Yet, even this approach fails in practical circumstances when high accuracy is required, as it assumes that the starting position and orientation of the magnet are accurately known and that the moves in a predictable manner. This assumption is unlikely to be true with respect to all magnets operably attached to the tissues of a given device. Inaccuracies can arise from deviations in magnet orientation, position, and/or motion from their assumed values.

In addition, a set of multiple magnets attached to tissues and moving simultaneously can result in a crosstalk phenomenon, wherein the magnetic fields resulting from movement of a tissue adjacent to the tissue of interest interfere with the measurements taken from that tissue of interest. All these sources of error individually or together can lead to significant inaccuracies and inconsistencies in the data acquired using this simplified methodology of the prior art, which can limit its utility in assessing tissue behavior, especially when compared with more conventional methods like optical microscopy-based analysis.

Other methods of magnetic sensing employed in applications such as the tracking of endoscopes (Su 2017) or prosthesis (Taylor 2019) are tailored to tracking of a few large magnets through a large volume. Such approaches perform sub-optimally when tracking sub-millimeter scale movements of magnets moving relatively close to the respective magnetic sensors (e.g., on the order of millimeters).

Accordingly, there is a need for improved magnetic localization devices and methods to overcome difficulties in tracking magnets operably attached to tissues cultured in vitro.

BRIEF SUMMARY

The devices and methods described herein overcome shortcomings of the prior art by allowing accurate, parallel measurements of the movement of magnets in a high throughput manner. For example, the devices and methods disclosed herein overcome limitations of the prior art systems by providing accurate, simultaneous tracking of any number of magnets, thereby enabling parallel measurements of motional changes of multiple tissues.

The present disclosure provides systems, devices, and methods for localizing magnets, including tissue analysis systems, tissue analysis devices, magnet localization methods, and computer program products storing instructions that cause the operation the magnet localization methods.

In an aspect, the present disclosure provides devices and methods (localization methods) for detecting motional, structural, or volumetric changes of three-dimensional biological tissues by tracking the location of magnets embedded therein with the use of an array of magnetic sensors and a magnetic model characterizing and iteratively simulating multiparametric positional information of a given set of moving magnets embedded in the tissues.

In an aspect, the present disclosure provides tissue analysis systems which include a tissue analysis device and a non-transitory machine readable storage medium storing instructions (a computer program product). The tissue analysis device includes at least one magnet and a plurality of magnetometers (a magnetometer array) disposed adjacent to each of the at least one magnet. For example, the tissue analysis device may include a plurality of magnets and a different magnetometer array disposed adjacent to each magnet. The storage medium stores instructions, which when executed by a processor, causes the tissue analysis system to perform operations, including, for each magnet: recording a magnetic field of the magnet with each magnetometer of the plurality of magnetometers; simulating a simulated magnetic field of a simulated magnet at each magnetometer of the plurality of magnetometers, wherein the simulated magnet has simulated positional information; and estimating positional information of the magnet based upon iterating the simulated positional information of the simulated magnet.

In another aspect, the present disclosure provides tissue analysis devices as described above.

In another aspect, the present disclosure provides tissue analysis systems for use with a tissue analysis device including at least one magnet and a plurality of magnetometers (a magnetometer array) disposed adjacent to each of the at least one magnet. The tissue analysis systems include a non-transitory machine readable storage medium storing instructions (a computer program product), which when executed by a processor, causes the performance of operations, including, for each magnet: recording a magnetic field of the magnet with each magnetometer of the plurality of magnetometers; simulating a simulated magnetic field of a simulated magnet at each magnetometer of the plurality of magnetometers, wherein the simulated magnet has simulated positional information; and estimating positional information of the magnet based upon iterating the simulated positional information of the simulated magnet.

In another aspect, the present disclosure provides magnet localization methods, which include: recording a magnetic field of a magnet at a plurality of locations (e.g., at one or more locations of each magnetometer of a magnetometer array); simulating a simulated magnetic field of a simulated magnet at the plurality of locations (e.g., at one or more locations of each magnetometer of a magnetometer array), wherein the simulated magnet has simulated positional information in theoretical space; and estimating positional information of the magnet based upon iterating the simulated positional information.

In another aspect, the present disclosure provides magnet localization methods, which include: recording a magnetic field of each magnet of a plurality of magnets with a nearest magnetometer array of a plurality of magnetometer arrays; simulating, at locations of each magnetometer array, a simulated magnetic field of a simulated magnet of a plurality of simulated magnets, wherein each simulated magnet has positional information; and estimating positional information for each magnet based upon iterating the simulated positional information of the simulated magnet at the nearest magnetometer array.

Any of the foregoing systems, devices, and methods include any one or more of the following optional features:

In any embodiment, iterating the simulated positional information of the simulated magnet may include iterating at least one of an x-position, a y-position, a z-position, a roll value, a pitch value, or a yaw value.

In any embodiment, iterating the simulated positional information of the simulated magnet may include iterating each of the x-position, the y-position, the z-position, the roll value, the pitch value, and the yaw value.

In any embodiment, estimating the positional information of the magnet may be based upon a cost function comparing the magnetic field and the simulated magnetic field.

In any embodiment, iterating the simulated positional information of the simulated magnet may include determining whether a solution that minimizes the cost function is from a first iteration of a cost minimization algorithm.

In any embodiment, iterating the simulated positional information of the simulated magnet may include iterating based upon simulated positional information from a previous iteration of a timepoint.

In any embodiment, iterating the simulated positional information of the simulated magnet may include iterating based upon simulated positional information associated with a previous timepoint or based upon nominal positional information.

In any embodiment, iterating the simulated positional information of the simulated magnet may include determining whether the value of the cost function meets termination criteria.

In any embodiment, estimating the positional information of the magnet may include comparing the magnetic field with the simulated magnetic field.

In any embodiment, each magnetometer of the plurality of magnetometers may include a plurality of magnetic sensing elements, and wherein recording the magnetic field may include sensing a flux density of the magnet with the plurality of magnetic sensing elements in each magnetometer.

In any embodiment, for each magnetometer, each magnetic sensing element may sense a different axis of the magnetic field (e.g., x, y, or z axis).

In any embodiment, the magnet may be disposed in an engineered tissue assembly and/or a tissue construct, and the plurality of magnetometers may be disposed upon a printed circuit board disposed adjacent to the engineered tissue assembly.

In any embodiment, the magnet may be one of a plurality of magnets of the tissue analysis device, wherein recording, simulating, and estimating may be performed for all magnets of the plurality of magnets.

In any embodiment, the instructions may be configured to record the magnetic field for each magnet at a different timepoint than for each other magnet.

In any embodiment, for each magnet, estimating the positional information may be based upon the simulated positional information of every magnet.

In any embodiment, estimating the positional information of the magnet may be performed at a plurality of timepoints and wherein the operations further comprise determining a positional change of the magnet between the plurality of timepoints.

In any embodiment, the operations may further include determining, based upon the positional change, a property of a tissue operably attached to the magnet.

Any embodiment may include a stimulation lid configured to move the magnet, and the operations may record the magnetic field of the magnet after or contemporaneously with movement of the magnet.

In any embodiment, estimating the positional information for each magnet may include iteratively varying the simulated positional information of all simulated magnets.

In any embodiment, the instructions or method may further include moving a plurality of tissues, wherein each tissue may be operatively attached to one magnet of the plurality of magnets.

In any embodiment, moving the plurality of tissues may include moving the plurality of tissues with temporally overlapping contractions.

In any embodiment, recording the magnetic field of each magnet may be performed at a different time than for each other magnet.

In any embodiment, recording the magnetic field of each magnet may include recording magnetic field data associated with different points in space.

In any embodiment, the instructions or method may further include determining an empirical relationship between the estimated positional information and recorded magnetic data and using the empirical relationship to estimate the positional information for a second plurality of magnets.

In any embodiment, estimating the positional information for each magnet may include adjusting for crosstalk based upon the recorded magnetic field of every other magnet of the plurality of magnets.

BRIEF DESCRIPTION OF THE DRAWINGS

Representative embodiments are described with reference to the following figures, wherein alike reference numerals refer to alike parts throughout the various views unless otherwise specified.

FIG. 8 schematically illustrates a twenty-four well map validating the efficacy of a magnet localization method according to an embodiment of the present disclosure.

DETAILED DESCRIPTION

The disclosed systems, devices, and magnet localization methods accurately track the motion of magnets, particularly in the context of relatively small magnets moving relatively close (single 10's of millimeter scale) to their respective magnetometers, e.g., in multi-magnet systems such as multi-well tissue analysis systems. In particular, the systems and methods account for different components of the magnetic field of each magnet at different locations, which more accurately reflects the actual properties of the magnetic fields being measured, rather than assuming all components are measured at a common location. Further, the systems and methods described herein account for differences in the position and movement of each magnet and also obviate the need to individually calibrate the measurement process for each magnet. These advantages result in higher accuracy and faster measurements.

The disclosed embodiments are generally described in the context of tissue analysis systems having a plurality of magnets, each being operably attached to a biological sample such as a tissue construct cultured in vitro, such as engineered muscle tissues including cardiac and skeletal EMTs. Such tissue analysis is particularly valuable for pharmaceutical studies and disease modeling. However, the systems and methods are limited to tissue analysis systems.

FIG. 1A-FIG. 1G show aspects of a tissue analysis system 100 of the present disclosure. The tissue analysis system 100 includes an array of magnetometers and an array of magnets, wherein a magnetometer array is positioned underneath each magnet. In the illustrated application, each magnet is embedded in a post of a two-post system wherein a biological sample such as a tissue construct can be cast and grown to be adhered between a pair of posts. Accordingly, the magnet is operably attached to the tissue. In other embodiments, the magnets may be operably attached to the tissue in other ways, for example mechanically affixed or adhered. The tissue analysis system 100 includes a plurality of such post pairs and an equivalent number of magnets and magnetometer arrays.

The magnetometer arrays of the tissue analysis system 100 are each configured to record, i.e., sense or detect magnetic fields emanated from magnets disposed in the immediate vicinity thereof, particularly a magnet disposed directly over the magnetometer array. Moreover, each magnetometer array is configured to sense the magnetic field at different locations and along different axes as the magnet(s) moves. Further, the tissue analysis system 100 includes software and/or firmware containing machine-readable logic or instructions that execute the magnet localization methods described herein based upon the recorded magnetic fields, which methods determine the location of the magnets in three-dimensional space.

Figure 1A:
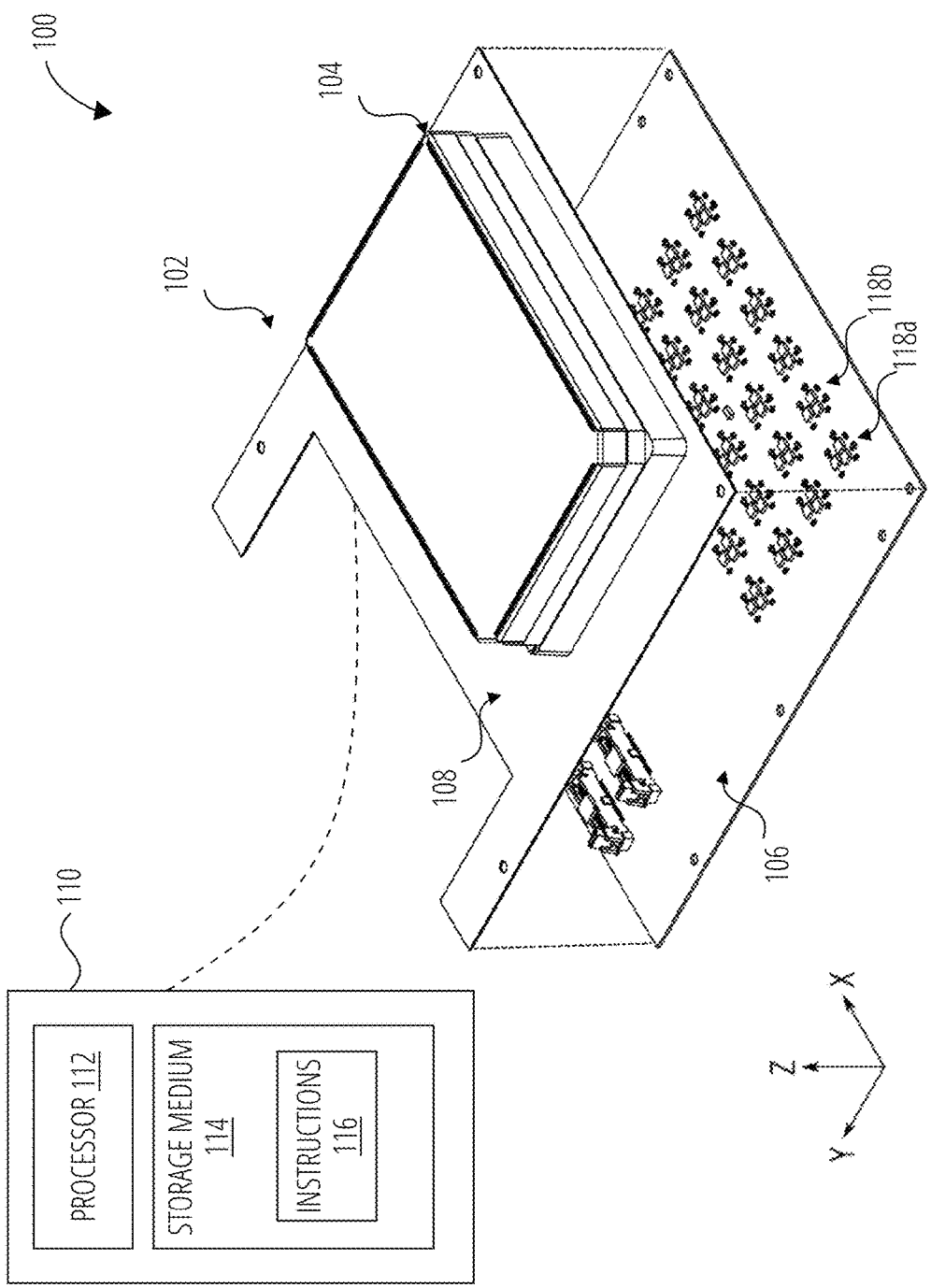
FIG. 1A illustrates a partially exploded view of a tissue analysis system according to an embodiment of the present disclosure.

Turning first to FIG. 1A, the tissue analysis system 100 includes a tissue analysis apparatus 102 having at least one magnet. In this example, the tissue analysis apparatus 102 includes a multi-well cartridge 104 with twenty-four wells, each well containing a magnet therein. The cartridge 104 is disposed atop a magnetometer board 106, e.g., a printed circuit board provided with a plurality of magnetometer arrays (e.g., 118a, 118b) as described below. As evident from FIG. 1B-FIG. 1F, each magnet in the cartridge 104 is disposed adjacent to one of the magnetometer arrays 118a. Each magnetometer of each magnetometer array 118a is configured to record a magnetic field emanated by the nearest magnet. Because magnetic ancillary components of the tissue analysis system 100 may alter or interfere with the field from the magnet under analysis, the magnetometers may be supported by passive components that do not incorporate magnetic materials, such as non-magnetic capacitors or resistors.

An optional magnetometer shield 108 is disposed between the magnets and the magnetometers of the magnetometer board 106. The magnetometer shield 108 may be formed of non-ferromagnetic metals including aluminum or brass, polymers such as acetal, poly-methyl-methacrylate, and polycarbonate, or other material excluding those with a ferromagnetic component, namely those containing iron, nickel, or cobalt.

Figure 10:
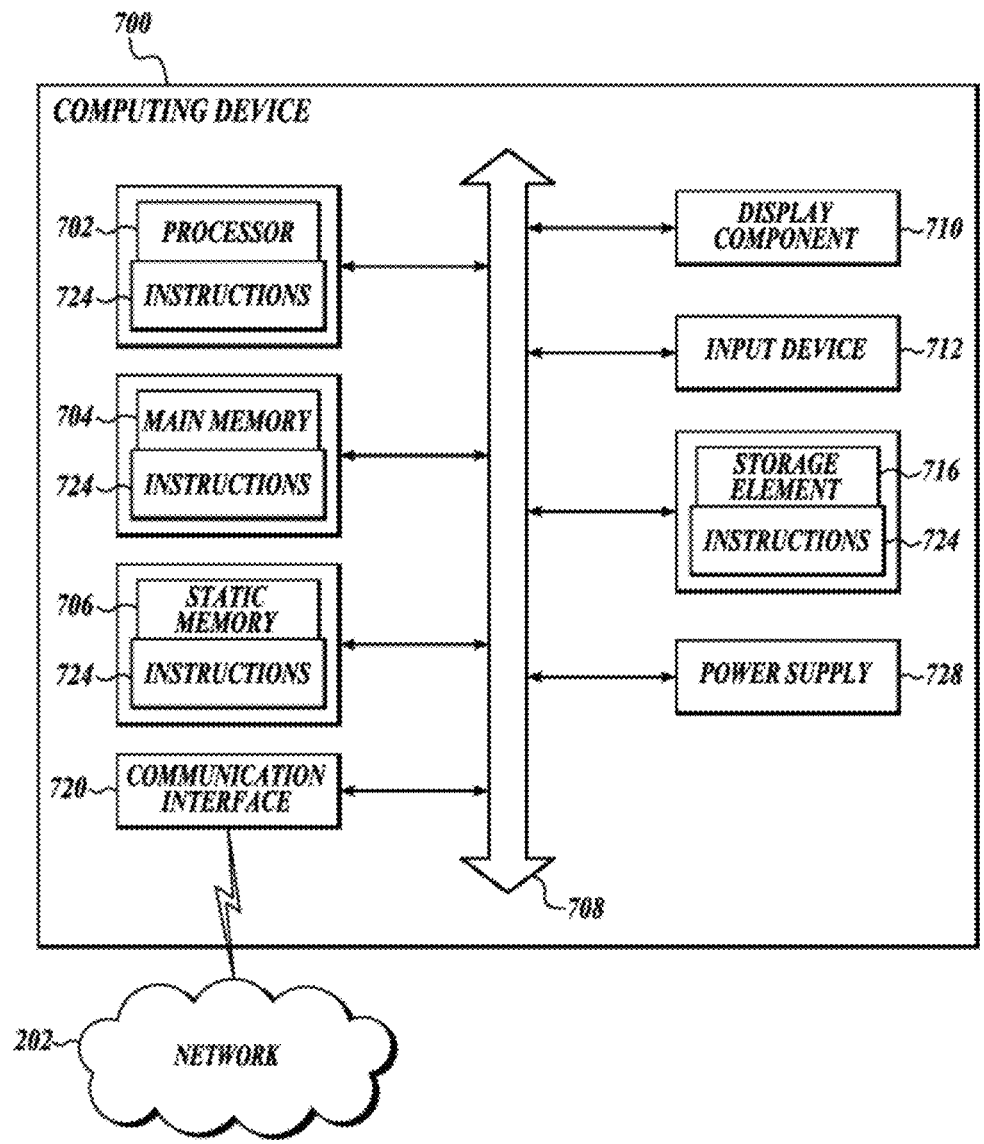
FIG. 10 shows a representative computing device configured to perform the methods described herein.

The tissue analysis system 100 may include or form part of a computing device 110 such as described with respect to FIG. 10. The computing device 110 may include a processor 112 and a non-transitory machine readable storage medium 114 storing one or more modules of computer-readable logic or instructions 116, which when executed by the processor 112, causes the processor 112 to perform operations, including any of the magnet localization methods and tissue analysis methods described herein. For example, the tissue analysis apparatus 102 may be an input device operably connected to the processor 112, and the instructions 116. More specifically, outputs from the tissue analysis apparatus 102, such as signals from magnetometers, may be inputs to the instructions 116 which implement the methods described herein.

The tissue analysis system 100 may be packaged within an enclosure of a larger apparatus having a power supply operably connected to a motherboard, the magnetometer board 106, a display, and an input device. Such apparatus may include an electrical stimulation lid and/or an electrical stimulation plate for applying electrical stimuli to the tissue constructs in the cartridge 104.

Figure 1B:
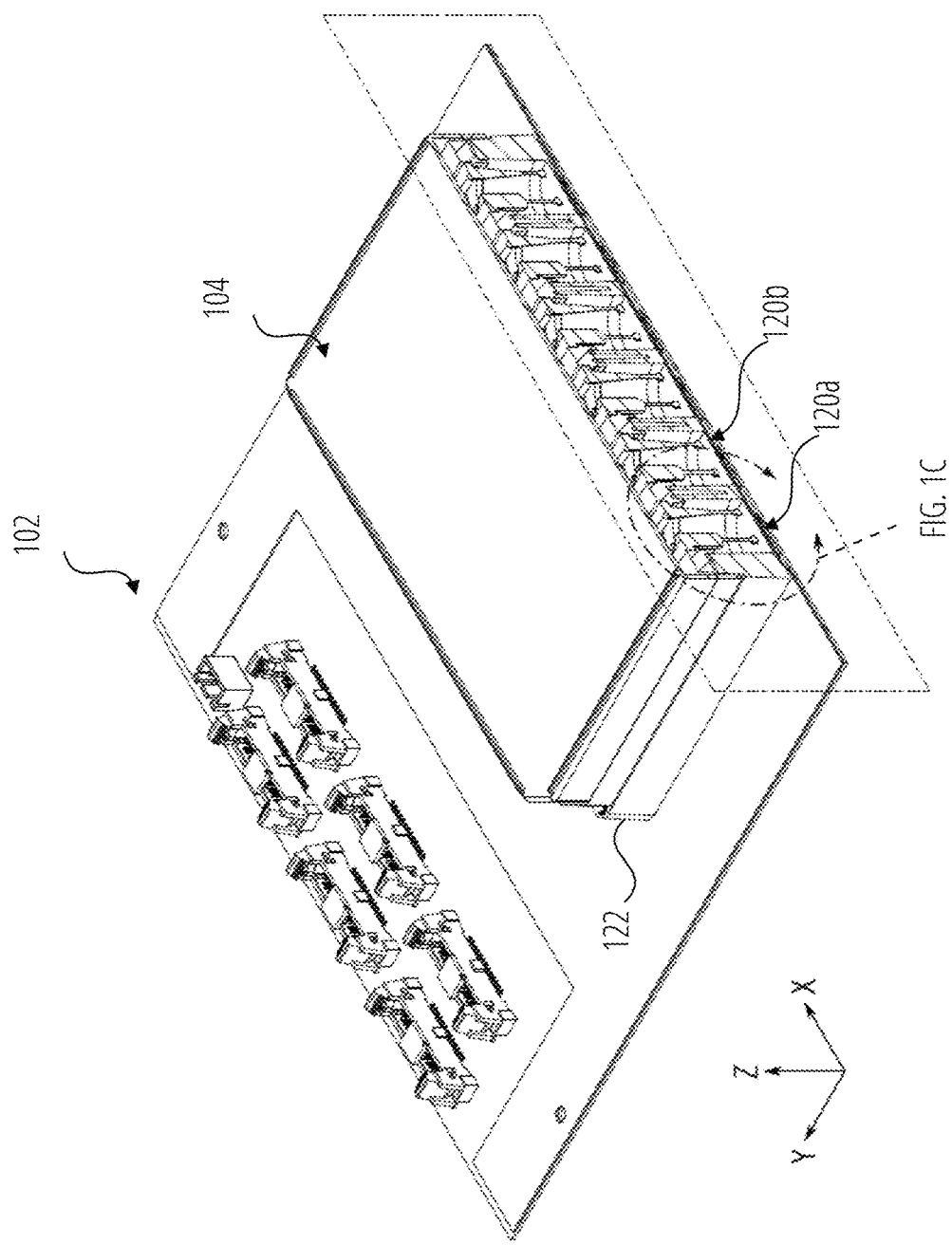
FIG. 1B illustrates a first section view thereof in the x-z plane.
Figure 1C:
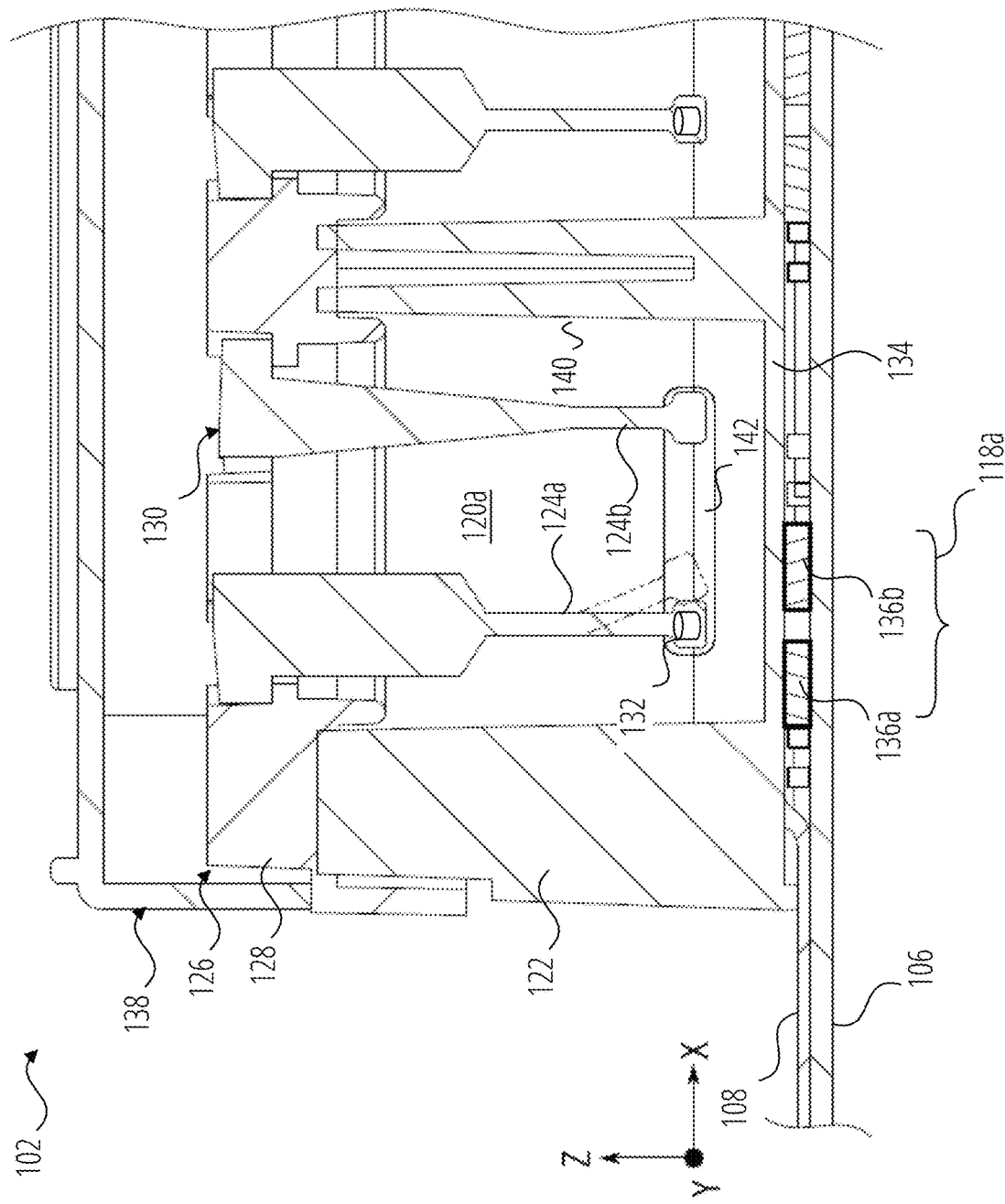
FIG. 1C illustrates a detail view of the first section view of FIG. 1B.

FIG. 1B illustrates a first section view of the tissue analysis apparatus 102 of FIG. 1A in the x-z plane. The cartridge 104 includes a plurality of wells (e.g., 120a, 120b) formed in a microplate 122, each well having a plurality of posts disposed therein. In the embodiment shown, the cartridge 104 includes twenty-four wells; however, other embodiments may have greater or fewer wells. As detailed below, each magnetometer array of the magnetometer board 106 is disposed directly underneath one of the wells in the z-direction. Because each well, magnetometer array, and post pair may be the same for all wells, a detail view is provided in FIG. 1C depicting one representative well 120a. In some embodiments, the microplate 122 may serve as a stimulation plate for applying electrical stimuli to the tissue constructs.

FIG. 1C illustrates a detail view of the section view of FIG. 1B in order to illustrate the relationship between one representative well 120a of the tissue analysis apparatus 102 and the magnetometer array 118a disposed thereunder.

The well 120a is formed as a recess in the microplate 122 having a cylindrical or frustoconical interior wall surface 140. A bottom surface 134 encloses the end of the well 120a nearest to the magnetometer board 106 and magnetometer shield 108.

An engineered tissue assembly 126 is fitted to an upper surface of the microplate 122 and includes a mounting lid 128 with a plurality of post assemblies 130 coupled thereto. Each post assembly 130 includes at least one post extending from a base thereof into a well. In particular, at least two posts extend from one or more post assemblies into each well, forming a post pair. For example, posts 124a, 124b form a post pair extending into well 120a.

In each well, one of the posts is a flexible post (e.g., an elastomeric flexible post) and the other post is relatively rigid, i.e., having a stiffness at least an order of magnitude greater than the flexible post. In well 120a, post 124a is a flexible post and post 124b is a rigid post.

A removable lid 138 covers the wells and post assemblies. The lid 138 may be a stimulation lid configured to apply electrical stimuli to a tissue construct 142 grown between the two posts 124a, 124b (e.g., an engineered heart tissue construct). The electrical stimuli cause the tissue construct 142 to move e.g., contract, which causes the flexible post 124a to bend, as shown.

A magnet 132 is embedded within or adhered to an outer surface of a distal end of the elastomeric flexible post 124a. The magnet may be a neodymium magnet, ferrite magnet, or other suitable magnet type. In the illustrated embodiment, the magnet 132 is oriented such that it has a magnetic dipole moment vector pointing along the x-direction.

To enable the magnet localization methods described herein, the magnetometer board 106 is configured and positioned such that one magnetometer array is disposed adjacent to each magnet of each well of the cartridge 104. For example, magnetometer array 118a is disposed directly underneath the magnet 132 in the z-direction and within about 1 mm to about 15 mm, e.g., about 2 mm to about 10 mm. In some embodiments, the magnetometer array (i.e., the magnetometers in the array) is positioned around the relevant magnet in the x-y plane (as shown in FIG. 1G).

Each magnetometer array may include two, three, four, or more magnetometers, each of which may include multiple magnetic sensing elements as described below with respect to FIG. 2A. For example, magnetometer array 118a includes magnetometers 136a, 136b, and 136c (see FIG. 1G), each positioned about 1 mm to about 15 mm away, e.g., about 2 mm to about 10 mm away from the magnet 132. In particular, each magnetometer of each magnetometer array is positioned and configured to detect a magnetic field of the nearest magnet. For example, magnetometers 136a, 136b are positioned at least partially on opposite sides of the magnet 132 in the x-direction and disposed about 1 mm to about 15 mm away, e.g., about 2 mm to about 10 mm away, therefrom in the z-dimension of the x-z plane. In the illustrated embodiment, at least two magnetometers of the magnetometer array 118a are aligned along a direction of the moment vector of the magnet 132—in this case, along the x-direction.

Figure 1D:
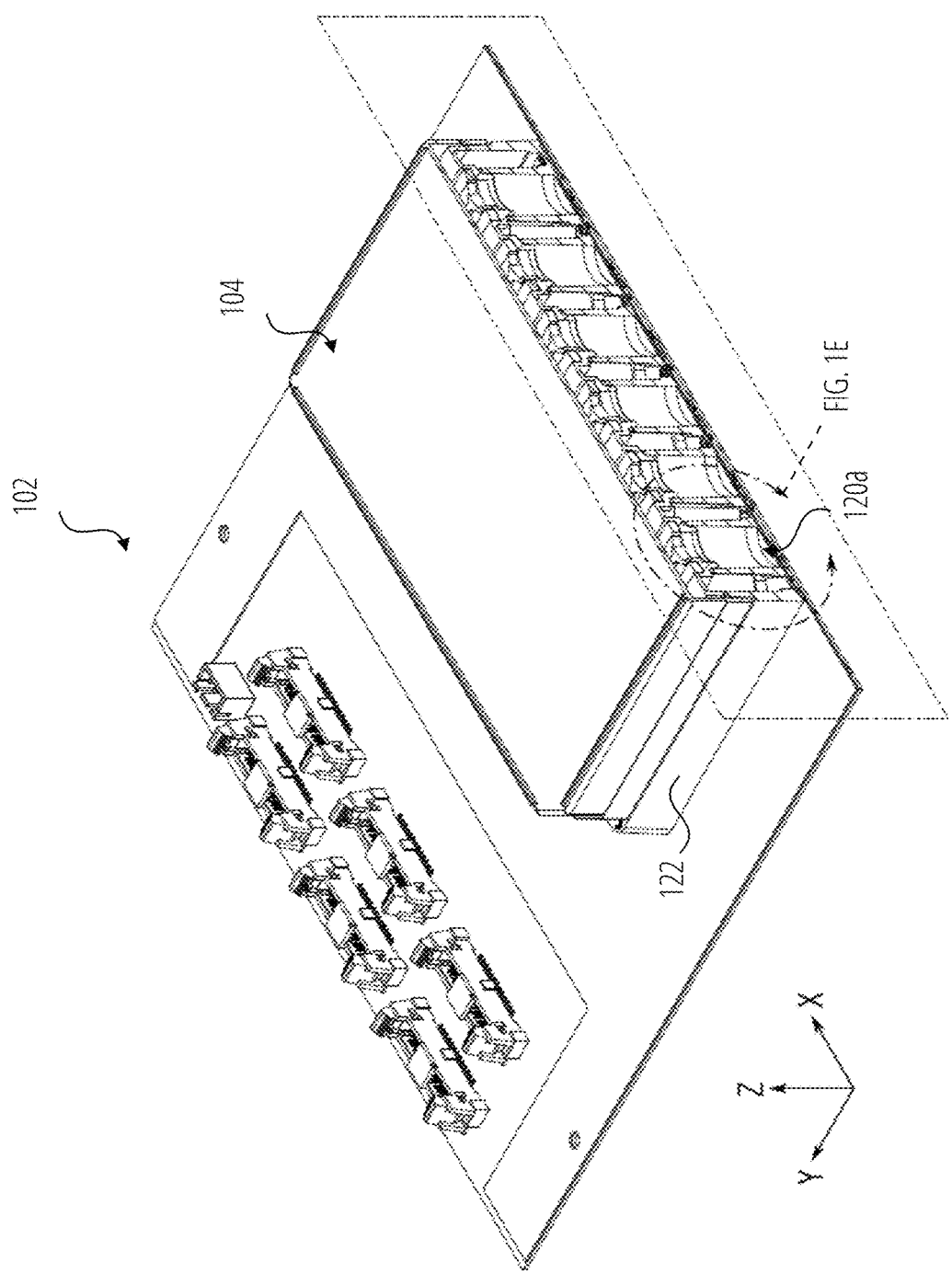
FIG. 1D illustrates a second section view of the tissue analysis system of FIG. 1A in the x-z plane.
Figure 1E:
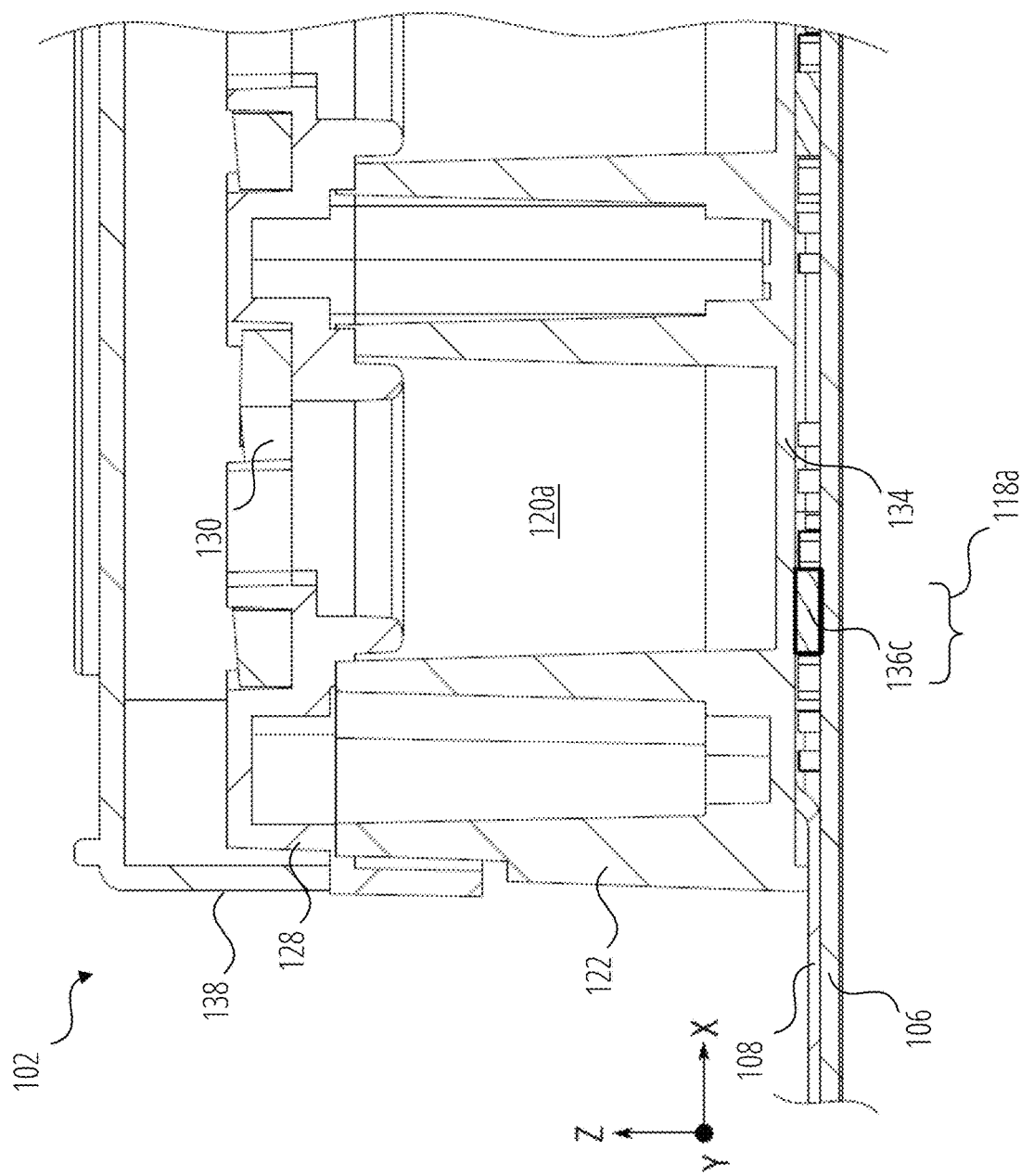
FIG. 1E illustrates a detail view of the second section view of FIG. 1D.

FIG. 1D illustrates a second section view of the tissue analysis apparatus 102 of FIG. 1A in the x-z plane. Relative to the section plane of FIG. 1B, the section plane of FIG. 1D is translated several millimeters in the positive direction along the y-direction. FIG. 1E depicts another detail view of the well 120a in order to illustrate additional features thereof.

FIG. 1E illustrates a detail view of the section view of FIG. 1D in order to further illustrate the relationship between the well 120a and the magnetometer array 118a disposed thereunder. The magnetometer array 118a includes the third magnetometer 136c which is also disposed underneath the well 120a and the magnet 132 in the z-direction.

Viewing FIG. 1C and FIG. 1E together, it is evident that all of the magnetometers 136a, 136b, 136c of the magnetometer array 118a are disposed underneath the magnet 132 in the z-direction.

Figure 1F:
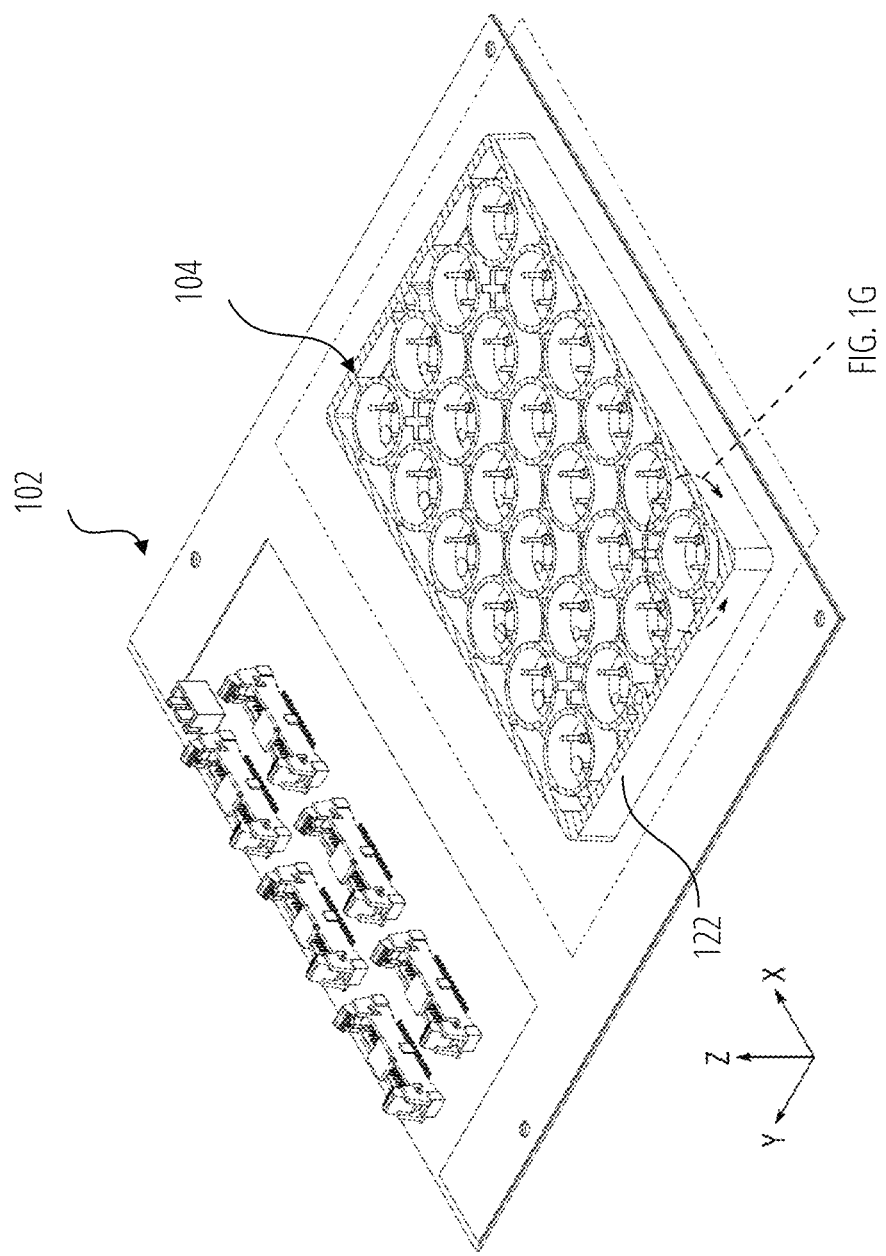
FIG. 1F illustrates a third section view of the tissue analysis system of FIG. 1A in the x-y plane.
Figure 1G:
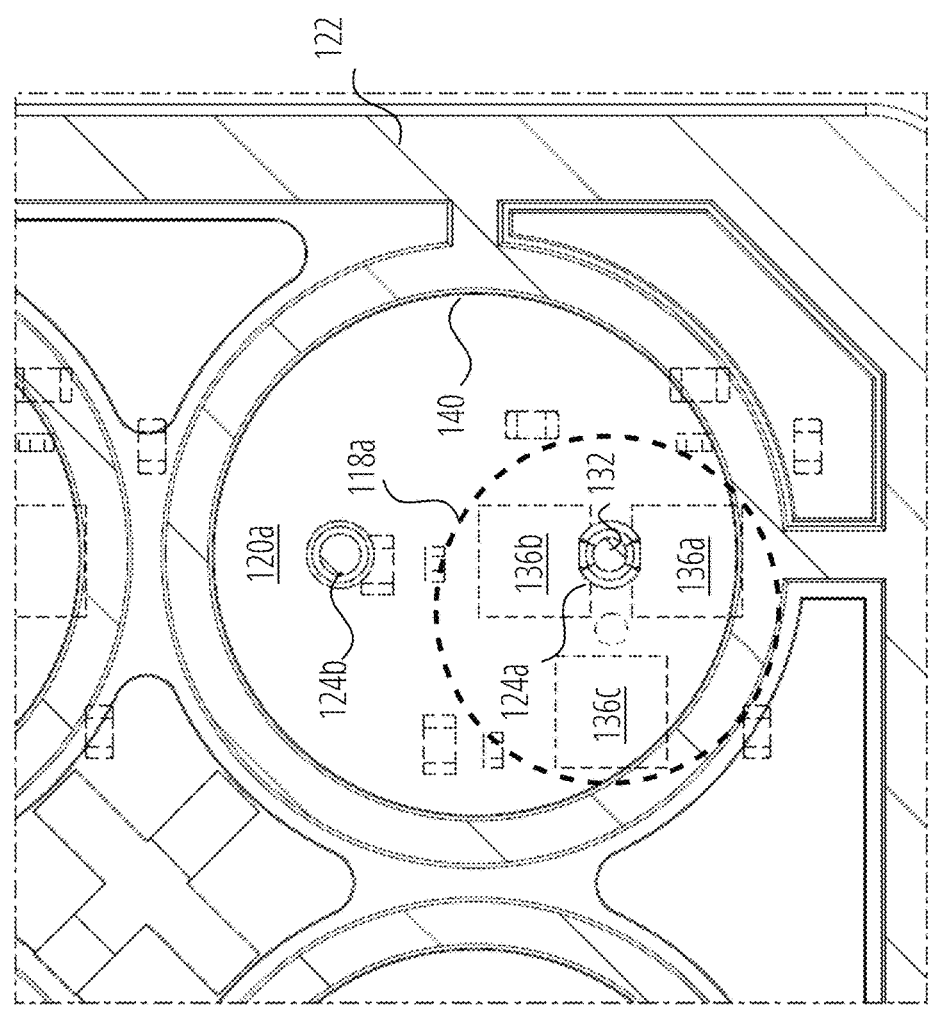
FIG. 1G illustrates a detail view of the third section view of FIG. 1F.

FIG. 1F illustrates a third section view of the tissue analysis apparatus 102 of FIG. 1A, in the x-y plane. As with FIG. 1C and FIG. 1E, FIG. 1G depicts another detail view of the well 120a in order to illustrate additional features thereof.

FIG. 1G illustrates another detail view of the section view of FIG. 1F and with the microplate 122 shown transparently in order to the magnetometer array 118a and to illustrate its spatial relationship with the well 120a its magnet 132.

As shown, the magnetometer array 118a includes a magnetometer cluster comprising magnetometers 136a, 136b, 136c disposed around the flexible post 124a (and the magnet 132) in the x-y plane. Centers of magnetometers 136a and 136*b* are offset by about 3 mm to about 5 mm and aligned along the x-direction with the dipole moment vector of the magnet 132.

A center of magnetometer 136*c* is offset by about 3 mm to about 5 mm from centers of the magnetometers 136*a*, 136*b* in the y-direction, i.e., the direction perpendicular to the magnetic moment vector of magnet 132.

In use, a tissue construct grown between the posts 124*a*, 124*b* will move (e.g., contract), causing the magnet 132 to move about +/−5 mm (e.g., +/− about 3 mm) in the x-direction and within about +/−3 mm (e.g., about +/−1 mm) in the y-direction. Application of an electrical current may cause the tissue to move, or the tissue may move spontaneously. As described below, the magnetometers 136*a*, 136*b*, 136*c* sense changes in the magnetic field of the magnet 132 at their respective locations caused by this movement.

Figure 2A:
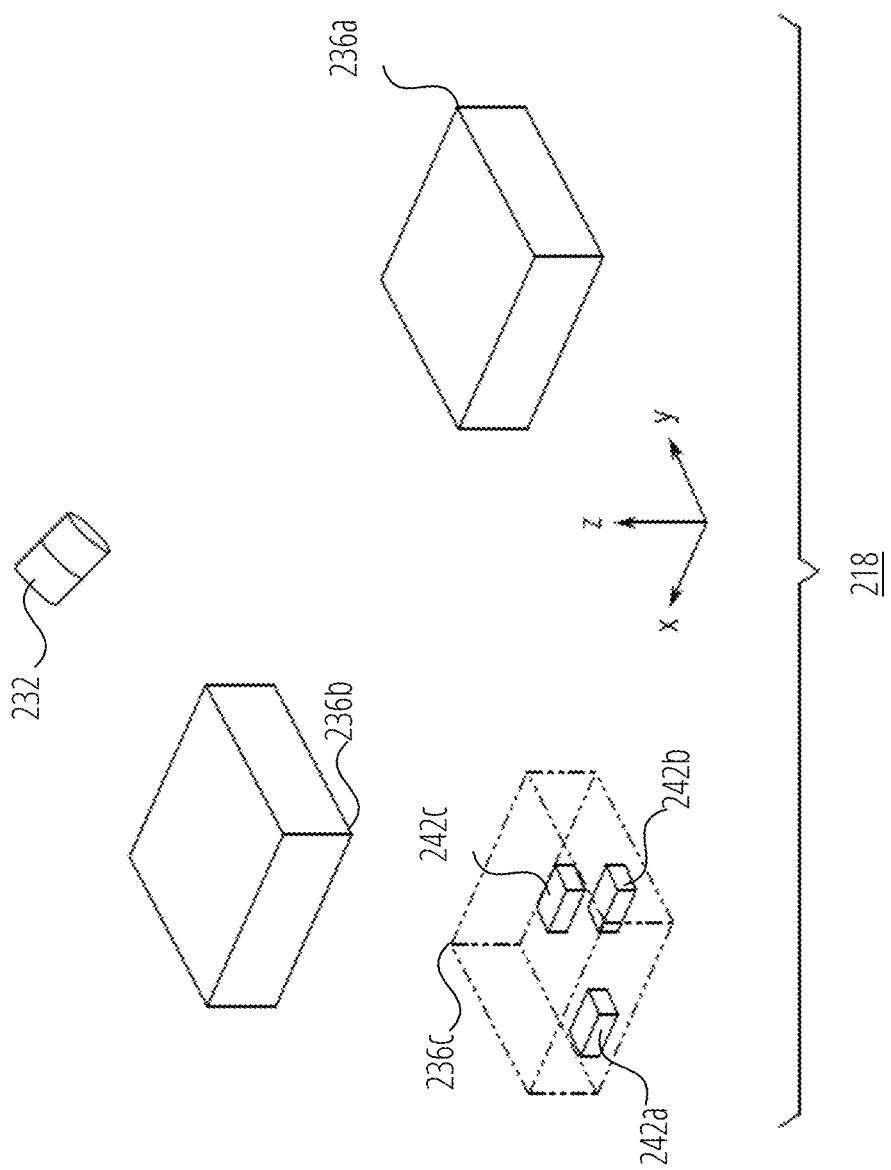
FIG. 2A schematically illustrates magnetometer array and magnet of a tissue analysis system according to an embodiment of the present disclosure.

FIG. 2A shows a three-dimensional layout of a magnetometer array 218 comprising a cluster of magnetometers 236*a*, 236*b*, 236*c* disposed around magnet 232. The magnetometer array 218 is the same as the magnetometer array 118*a* of FIG. 1A-FIG. 1G.

Magnetometer 236*c* is shown with its outer packaging rendered transparent in order to reveal magnetic sensing elements 242*a*, 242*b*, 242*c*. As used herein a magnetic sensing element is an element (such as a ferromagnetic element) that measurably changes one or more properties when subjected to one or more components of the flux density of an applied magnetic field. The magnetometer 236*c* measures the relevant properties of the magnetic sensing elements 242*a*, 242*b*, 242*c* to determine the magnetic field component (of the magnet 232) over a particular area or volume, e.g., an average magnetic field component, and to output signals communicating magnetic field data based upon the recorded magnetic field.

For example, each of the magnetic sensing elements 242*a*, 242*b*, 242*c* is configured to record the magnetic flux density of the magnetic field emanated by magnet 232 along the x, y, or z axis, respectively. Magnetometers 236*a* and 236*b* are identical to magnetometer 236*c*. Accordingly, each of the plurality of magnetometers includes a plurality of discrete magnetic sensing elements. Thus, in the illustrated embodiment, the magnetometer array 218 senses the magnetic field from magnet 132 at nine different points in space. Representative magnetometers include anisotropic magnetoresistance sensors (for example, model MMC5983MA manufactured by Memsic Semiconductor Co., Ltd. of Tianjin, China), fluxgates, Hall sensors, giant magnetoresistance or tunneling magnetoresistance sensors.

The inclusion of a plurality of magnetic sensing elements at different positions in each magnetometer is particularly advantageous. It is commonly assumed that magnetic sensing elements within a magnetometer overlap each other perfectly, and that all components of the magnetic field are sampled at the same location. However, this assumption fails when magnets are positioned close to the magnetometer, as in the tissue analysis systems and magnet localization methods described herein, since the distances between magnetic sensing elements are large enough relative to the distances between the magnetic sensing elements and the magnets to cause the magnetic sensing elements to experience appreciably different fields than if they perfectly overlapped. The magnet localization methods of the present disclosure may account for this feature of the magnetometer arrays mathematically by deriving each component of the magnetic field from the scalar product of simulated magnetic fields and by unit vector $\hat{k}_s$, defined in accordance with the directional sensitivity of the magnetic sensing element at which fields are being simulated.

The magnetometers 236*a*, 236*b*, 236*c* are positioned around the magnet 232 (e.g., within about 1 mm to about 15 mm or about 2 mm to about 10 mm) in order to record the magnetic field of the magnet 232, e.g., once the magnet 232 is placed in a specific position in relation to the magnetometers.

The magnetometer array 218 is positioned to optimize the magnet localization accuracy and signal-to-noise performance of magnetic field recordings. In addition to the magnetic sensing elements, each magnetometer may have additional components for filtering, amplifying, or otherwise processing and/or digitizing the output of the magnetic sensing elements therein. The output of each magnetometer may optionally be communicated to additional elements of a signal chain that terminates when the magnetic field data achieves a state that can be properly incorporated into any of the magnet localization methods described herein to enable further processing by a computational algorithm that extracts the desired information regarding the magnets in the system.

The foregoing arrangement for a single magnetometer array 218 and magnet 232 may be repeated for every magnet of a multi-magnet system, e.g., the tissue analysis system 100 of FIG. 1A.

Figure 2B:
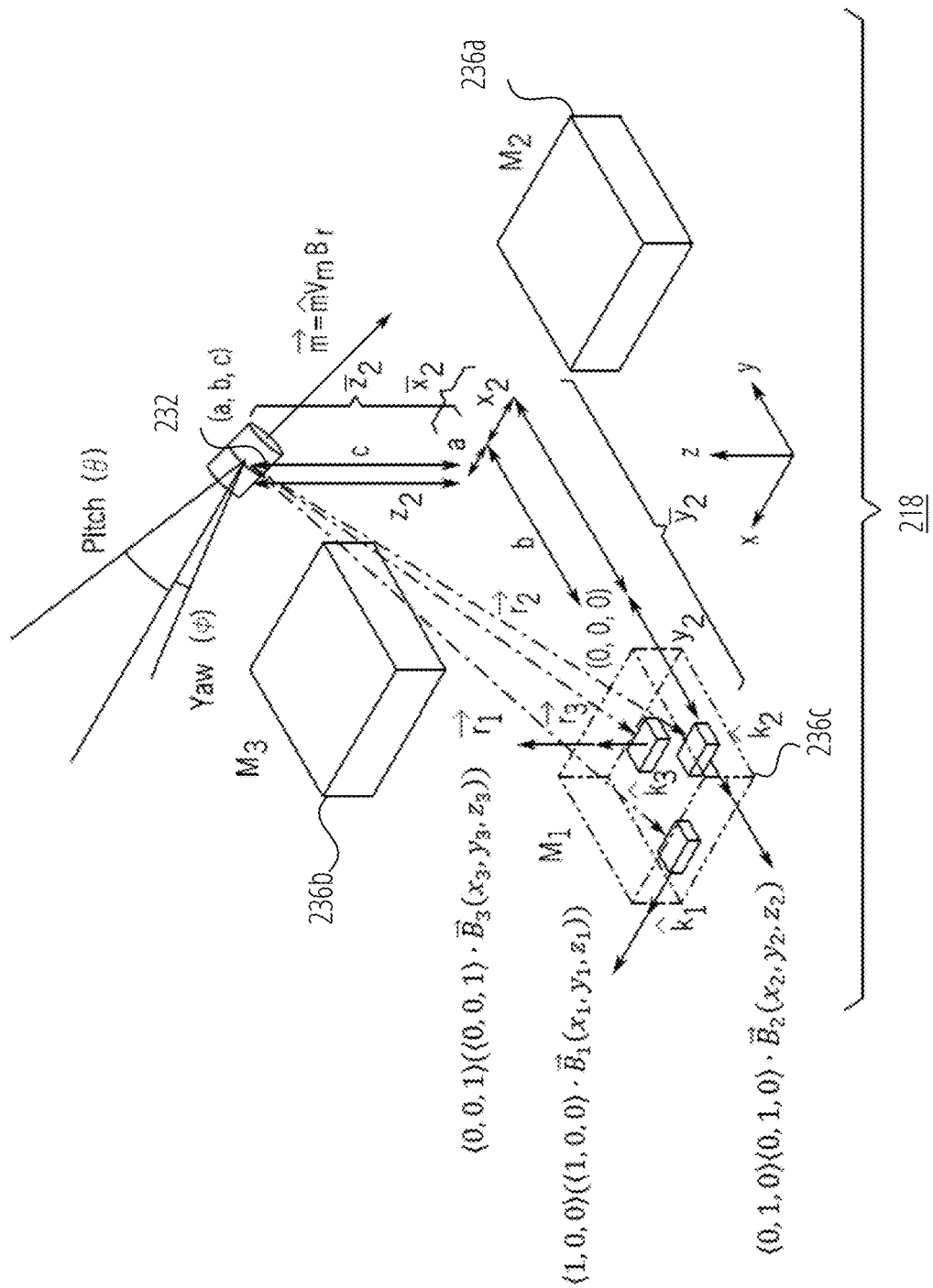
FIG. 2B illustrates geometric parameters thereof.

FIG. 2B defines geometric parameters of the magnet localization methods in relation to the magnetometer array 218. Bidirectional arrows indicate scalar distances, unidirectional arrows indicate vector quantities. Subscripts refer to a specific magnetic sensing element unless subscripting the letter "M" in which case the subscript numbers magnetometers.

The magnet localization methods utilize a computational model of magnetic behavior in conjunction with the magnetic field data acquired from the magnetometers (e.g., magnetometers 236*a*, 236*b*, 236*c*) to quantify the following positional information of one or more adjacent permanent magnets (e.g., magnet 232) in three-dimensional space with respect to an arbitrary reference point, as shown in FIG. 2B:

x-position (a)

y-position (b)

z-position (c)

roll value, or rotation about y axis with respect to the magnet's center line pitch value ($\theta$), or rotation about x axis with respect to the magnet's center line yaw value ($\phi$), or rotation about z axis, orthogonal to the x axis and the magnet's center line residual magnetic flux density $\vec{B}_r$ The foregoing parameters may also characterize positional information of one or more simulated magnets, which parameters are inputs into the equations described below.

Figure 2C:
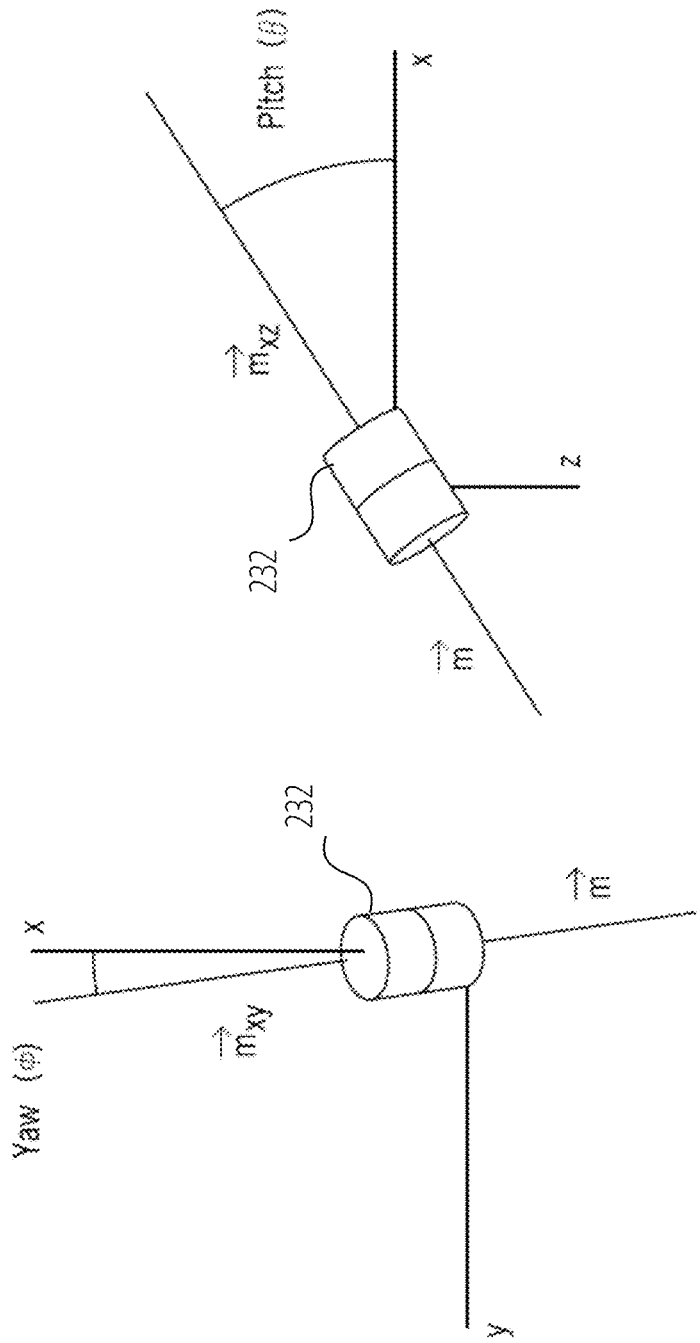
FIG. 2C illustrates additional parameters thereof.

FIG. 2C illustrates rotations of the magnet 232 in the x-y and x-z planes, respectively referred to as pitch ($\theta$), or yaw ($\phi$). $\vec{m}_{xy}$ indicates the projection magnetic moment of the magnet onto the x-y plane, and $\vec{m}_{xz}$ indicates the projection of the magnetic moment in the x-z plane.

With the foregoing parameters defined, the principles of the magnet localization methods will now be introduced prior to describing the representative methods.

The magnet localization methods generally involve computationally simulating a magnetic field of at least one simulated magnet, e.g., at a location of one or more magnetometers. The simulated magnet may be modeled as a magnetic dipole, which has been empirically demonstrated to be accurate when estimating magnetic fields at distances from the magnet on the order of a few hundred percent of its characteristic dimension, as described with respect to the tissue analysis system 100 of FIG. 1A-FIG. 1G. Other embodiments may incorporate other analytical or numerically approximated models of magnetic behavior, such as those for cylindrical, spherical or cuboid models. To facilitate understanding, the magnetic dipole model is described herein as one suitable representative and non-limiting model.

In the magnetic model the following equation can be used to simulate the magnetic field, e.g., flux density $\vec{B}\left(\vec{r}, \vec{m}\right)_{model}$ of the simulated magnet, at points in $\mathbb{R}^3$ surrounding the dipole with magnetization vector $\vec{m}$ at distance $\vec{r}$, where $\mu_0$ represents the magnetic permeability of vacuum.

$$\vec{B}(\vec{r}, \vec{m})_{model} = \frac{\mu_0}{4\pi} \frac{3\hat{r}(\hat{r}\cdot\vec{m}) - \vec{m}}{|\vec{r}|^3} \quad (1)$$

Cartesian coordinates corresponding to a location of the simulated magnet are used to estimate the real-world position of magnet 232 and/or post deflection. If a, b, and c respectively correspond to the x, y, and z-position of the simulated magnet relative to a global reference point (0, 0, 0), then the magnetic field B from the simulated magnet at point (a, b, c) at point (x, y, z) relative to that same reference point is:

$$\vec{B}(x, y, z, a, b, c, \theta, \phi, B_r, V_m)_{model} = \quad (2)$$

$$\frac{V_m B_r \mu_0}{4\pi} \left[ \frac{3(\bar{x}, \bar{y}, \bar{z})(\bar{x}\sin\theta\cos\phi + \bar{y}\sin\theta\sin\phi + \bar{z}\cos\theta)}{\sqrt{\bar{x}^2 + \bar{y}^2 + \bar{z}^2}^5} - \frac{(\sin\theta\cos\phi, \sin\theta\sin\phi, \cos\theta)}{\sqrt{\bar{x}^2 + \bar{y}^2 + \bar{z}^2}^3} \right]$$

In equation (2), $\bar{x}, \bar{y}$, and $\bar{z}$ are defined as (x−a), (y−b) and (z−c), respectively, where $\theta$, $\phi$ and $B_r$ correspond to its pitch, yaw, and residual flux density, where $V_m$ is the magnet volume. Using equation (2), simulated magnetic fields at locations that match the magnetometer positions can be simulated for each simulated magnet i of n simulated magnets in the system, e.g., simulated magnets corresponding to magnet 232 and every other real-world magnet.

Characterizing each simulated magnet i of n simulated magnets in the system in theoretical space with position ($a_i$, $b_i$, $c_i$), pitch and yaw ($\theta_i$, $\phi_i$) and residual flux density $B_{r,i}$, for the field at a magnetic sensing element $B_s$ at point ($x_s$, $y_s$, $z_s$) measuring the magnetic field component along unit vector $\hat{k}_s \in \mathbb{R}^3$ is given by:

$$B_{s,model} = \hat{k}_s \cdot \sum_{i=1}^{n} B(x_s, y_s, z_s, a_i, b_i, c_i, \theta_i, \phi_i, B_{r,i}, V_{m,i})_{model} \quad (3)$$

In comparison to known methods which assume, for example, that three components of a magnetic field are sensed at a single location, equation (3) accounts for each component of the magnetic field (e.g., the x-component, y-component, and z-component) at different locations. Advantageously, this accounts for the failure of assumptions in prior art methods when the sensed magnets are disposed relatively close to the magnetometer.

As described above, $\hat{k}_s$ is a vector of unit length, defined in accordance with the directional sensitivity of the real-world magnetic sensing element at which the fields are being simulated. As shown in FIG. 2B, $\hat{k}_s$ points along one of three orthogonal axes that form a basis for $\mathbb{R}^3$.

Simulated magnetic field values at all magnetometer locations in the system can be arranged into the vector $\vec{B}_{model}$. Likewise, readings from the real-world magnetometers (e.g., magnetometers 236a, 236b, 236c) at those same points in space of the same field components generated by real-world magnets (e.g., magnet 232) can be arranged into the vector $\vec{B}_{measured}$ Since the magnets in the tissue analysis systems described herein may operate close to the respective magnetometers (on the order of millimeters), the magnetometers may be physically large enough such that the magnetic field over the magnetometer and its magnetic sensing elements may be not be effectively constant or linearly varying in space. In such cases, values within $\vec{B}_{model}$ and $\vec{B}_{measured}$ may give average magnetic fields over the area or volume of the magnetometer.

A mathematical function may be utilized to compare the two vectors, i.e., comparing the simulated magnetic fields with the real-world magnetic fields. For example, one representative function, $\vec{B}_{residual}$ is:

$$\vec{B}_{residual} = \vec{B}_{model} - \vec{B}_{measured} \quad (4)$$

The function may be iteratively computed according to a minimization algorithm, in order to determine the "best" or sufficient solution for magnet parameters of interest. For example, one or more parameters of the simulated positional information may be iteratively changed until the value of the function is minimized or otherwise meets certain termination criteria.

For example, if the minimization algorithm is compatible with the least squares method, then by minimizing the $l^2$-norm of this function, $|\vec{B}_{residual}|$, otherwise known as a possible cost function for the problem, by adjusting simulated positional information, e.g., $a_i$, $b_i$, $c_i$, $\theta_i$, $\phi_i$, and $B_{r,i}$ for all magnets in the system, real-world positional information, i.e., the position and orientation of each real-world magnet in the system can be estimated.

Although the least squares method is described as one representative cost minimization algorithm to compare the simulated magnetic fields with the real-world magnetic fields, other suitable minimization approaches include those for performing such non-linear regression. Minimization may be implemented by algorithms such as the Levenberg-Marquardt and Trust-Region Reflective algorithms.

Having described principles of the methods, details of the magnet localization methods will now be described.

Any step described below is optional unless stated otherwise, and embodiments of the present disclosure may include any combination of the following steps. Further, any step or combination of steps described below may be implemented as instructions on a non-transitory machine readable storage medium. For example, the methods described below may be implemented as one or more software or firmware instruction modules for execution by a processor in connection with a tissue analysis system.

Figure 3:
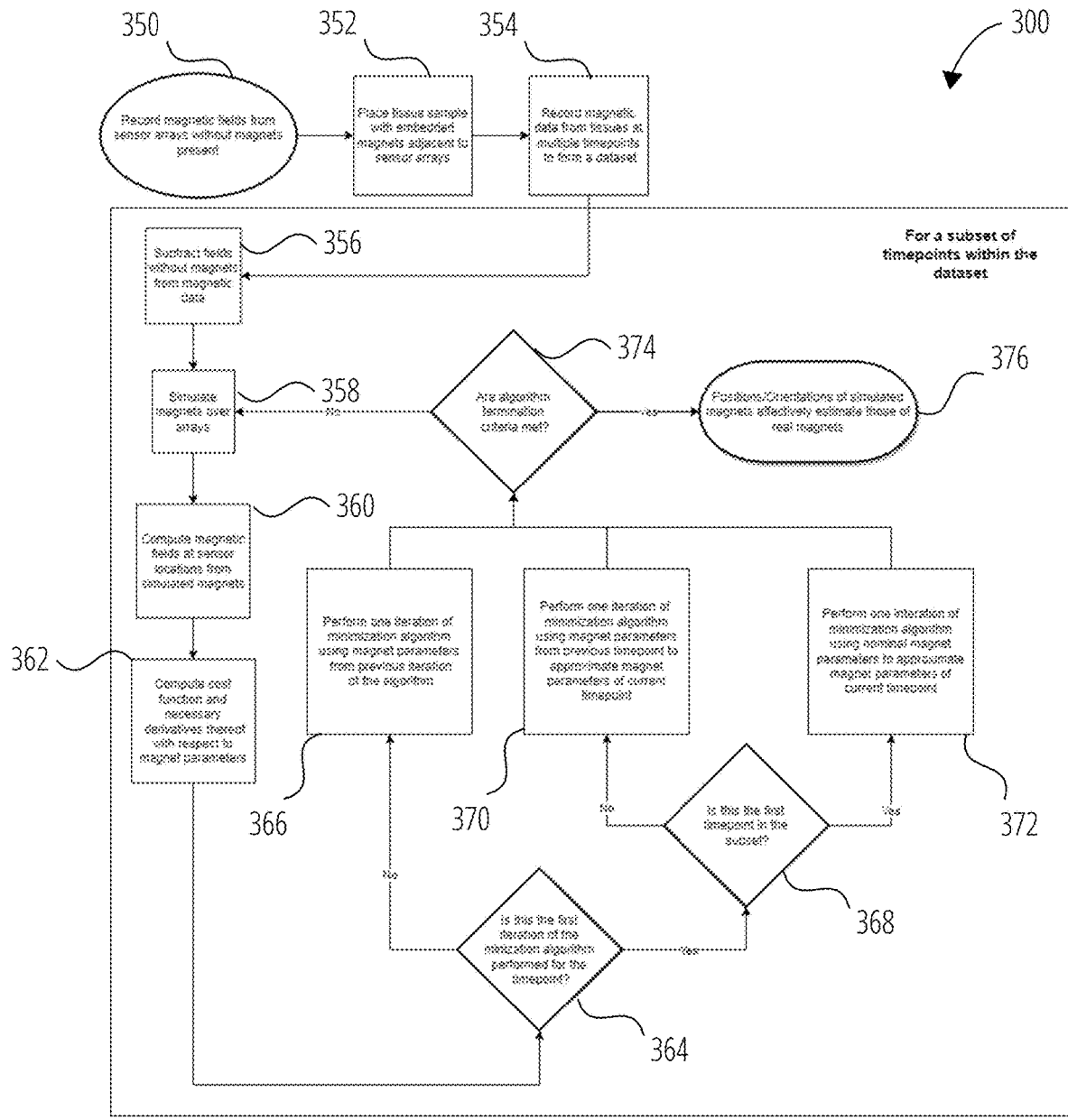
FIG. 3 schematically illustrates a magnet localization method according to an embodiment of the present disclosure.

FIG. 3 depicts representative magnet localization methods 300 by which iterative magnetic modeling is used to accurately estimate positional information of one or more real-world magnets in a system. Generally, for each magnet in the system, the magnet localization methods 300 record the magnetic field of that magnet, and then simulates the magnetic field of a simulated magnet having simulated positional information. The method compares the recorded magnetic field of the real-world magnet with the simulated magnetic field of the simulated magnet, then iterates the positional information of the simulated magnet until a comparison between the real-world magnetic field and the simulated magnetic field satisfy termination criteria, whereupon the simulated positional information of the simulated magnet is an accurate estimation of the positional information of the real-world magnet.

One representative method depicted in FIG. 3 will now be described. Any of the following steps may be computed by a special purpose computing device such as a processor of the tissue analysis system described herein.

To facilitate understanding, the magnet localization method 300 is described in the context of the tissue analysis system described with respect to FIG. 1A-FIG. 2C. Accordingly, the terms used to describe the following method have the same meanings as previously introduced. In any embodiment, the steps of the following methods may be performed in a tissue analysis system having any of the physical characteristics described above, e.g., number of magnetometers, magnetometer spacing, magnetometer alignment, etc. However, the following methods are not limited to this application, and may be performed independently of tissue analysis systems.

The magnet localization method 300 applies both to single magnet systems and multi-magnet systems at a plurality of timepoints. In multi-magnet systems, the following steps may be performed for each magnet in the system or a subset of magnets in the system, e.g., contemporaneously or sequentially, in order for the recording and simulating steps described below to accurately account for all magnets (or the relevant subset) of the underlying system. With this understanding, the following steps are generally described for a single magnet for clarity.

Optionally, a system including a plurality of magnets and a plurality of magnetometer arrays may be initially provided, e.g., a tissue analysis system.

At step 350, as part of an optional calibration sequence, local magnetic field data are recorded, e.g., without magnets present. The local magnetic field data may be influenced by the Earth's geomagnetic field, a magnetometer array and/or magnets of an underlying system, and other factors. For example, in a tissue analysis system, local magnetic field data may be recorded with each magnetometer of the magnetometer array 118a without the magnet 132 present, such as when the cartridge 104 containing the magnet 132 is removed from the magnetometer board 106 or the magnets 132 is otherwise removed from the immediate vicinity of the magnetometer array 118a.

At step 352, a magnet is placed adjacent to a magnetometer array. The magnet may be positioned such that magnetometers of the adjacent magnetometer array are disposed around the magnet and/or within about 1 mm to about 15 mm or about 2 mm to about 10 mm from the magnet. The magnet may be positioned to align its magnetic moment vector with two or more magnetometers of the magnetometer array along an axis. For example, a cartridge 104 containing a plurality of magnets may be positioned adjacent the magnetometer board 106 having a plurality of magnetometer arrays 118a thereon such that each magnet is disposed adjacent to, e.g., within about 1 mm to about 15 mm or about 2 mm to about 10 mm, one of the magnetometer arrays.

At step 354, device magnetic data (e.g., magnetic field data) is recorded for the magnet. For example, a magnetic field of a magnet 132 of a tissue analysis system 100 may be recorded concurrently with a plurality of magnetometers 136a, 136b, 136c of a magnetometer array 118a. The device magnetic data may include the flux density of the magnetic field of the magnet along the x, y, and/or z axis at different locations, e.g., as sensed by magnetic sensing elements of magnetometers of a magnetometer array. Each of the x, y, and/or z axis components of the magnetic field may be sensed at a plurality of locations, e.g., with different magnetometers of the magnetometer array, in order to record the magnetic field at different points in space. In multi-magnet systems, the device magnetic data for each magnet may be recorded at a different timepoint than for each other magnet.

Step 354 may include moving at least one tissue (e.g., tissue construct) attached to the magnet before or contemporaneously with recording the device magnetic data of the magnet. Each tissue construct may be moved, e.g., contracted, by an electrical stimulus applied to the tissue construct or a surrounding medium. In multi-magnet systems, moving at least one tissue may include moving a plurality of tissues with temporally overlapping contractions.

The device magnetic data for the magnet or all magnets may be compiled into a first vector.

At step 356, as a further step in the optional calibration sequence, the local magnetic field data recorded at step 350 are subtracted from the device magnetic data, e.g., element-wise according to x, y, and z components. This adjusts for magnetic fields arising from the earth or adjacent permanent magnets or electrical currents that are not accounted for in the following magnet localization method. Subtracting the local magnetic field data may include subtracting one or more time points or time-averages of the local magnetic field data for different timepoints from the device magnetic data. For example, in some embodiments, a first time series of local magnetic field data recorded at step 350 is subtracted from a second time series (of equal length) of device magnetic data recorded at step 354, in order to arrive at adjusted magnetic fields for each time point. In other embodiments, an average of the time series of local magnetic field data is subtracted from the device magnetic data recorded at step 354. As used herein, device magnetic data includes both adjusted and unadjusted device magnetic data.

At step 358, a magnet is simulated at a point in theoretical space over the magnetometer array, for example by assuming simulated positional information including at least one of a simulated position (Cartesian coordinates), simulated orientation, a magnetic flux density, and/or a volume of the simulated magnet. Herein, such a magnet in theoretical space is referred to as a "simulated magnet". The point in space may be disposed over the magnetometer array along at least one of the x, y, and/or z directions. The point in space may be arbitrary, a best estimate, based upon simulated positional information from a previous timepoint and/or from a different magnet. The simulated position may be characterized by an x-position, a y-position, and/or a z-position, and the orientation may be characterized by a pitch value and/or a yaw value.

Step 360 simulates a simulated magnetic field of the simulated magnet based upon the simulated positional information, as described above with respect to FIG. 2A-FIG. 2C, and prepares simulated magnetic field data therefrom. The simulated magnetic field may include directional components and may be simulated at locations that match each of the plurality of magnetometers of the closest magnetometer array (or even each of the magnetic sensing elements thereof). The simulated magnetic field may be simulated at the location of one or more additional magnetometer arrays (e.g., at the location of all magnetometers of all magnetometer arrays).

For example, the simulated magnetic field may be computed using equations such as equations (1)-(3) introduced above. Simulating the simulated magnetic field may be based upon a magnetic dipole model, a cylindrical magnetic model, a spherical magnetic model, a cuboid magnetic model, or other magnetic model. Simulating the simulated magnetic field may include simulating a flux density of the simulated magnet at points in space surrounding simulated magnet, e.g., with a magnetization vector and at a distance. Simulating the simulated magnetic field may include taking the scalar product of the simulated magnetic field and a unit vector defined in accordance with a directional sensitivity of the magnetic sensing element at which locations the fields are being simulated.

The simulated magnetic field data for the simulated magnet or for all simulated magnets may be compiled into a second vector.

Subsequent to step 360, the magnet localization method 300 includes estimating positional information for the real-world magnet including at least one of a position, an orientation, or a magnetization thereof based upon the simulated positional information of the corresponding simulated magnet (or optionally based upon all simulated magnets). Estimating the positional information compares the device magnetic data with the simulated magnetic field data and is based upon one or more functions as described below. The estimating step includes any one or more of the following steps.

At step 362, a cost function is solved or computed for one or more timepoints in the device magnetic data to compare the device magnetic data with the simulated magnetic field data. The cost function may compare the first vector (which is based upon the device magnetic data) with the second vector (which is based upon the simulated magnetic field data). The cost function may be a one-dimensional mathematical function. One representative cost function is described above with respect to equation (4). Derivative entities of the cost function, such as its Jacobian matrix, may also be computed to assist in later steps of the process.

To accurately estimate the positional information of the magnet(s), the cost function may be computed repeatedly by iterating the simulated positional information of the simulated magnet, for example by using a minimization algorithm such as the least squares method, implemented by the Levenberg-Marquardt algorithm, or Trust-Region Reflective algorithms, until its value is minimized or otherwise meets termination criteria. Accordingly, the methods provide the following iterative solution procedure.

Step 364 includes determining whether the cost function solution of step 362 is the solution from a first iteration of a cost minimization algorithm.

If the answer to step 364 is negative, then the magnet localization method 300 proceeds to step 366, whereby the minimization algorithm iterates based upon at least one parameter of the simulated positional information from a previous iteration of a same timepoint of the device magnetic data, in order to minimize the cost function for the same timepoint again. Iterating may include updating at least one, or all, of an x-position, a y-position, a z-position, a roll value, a pitch value, or a yaw value of the simulated positional information from a previous iteration of the same timepoint.

Alternatively, if the answer to step 364 is affirmative, then the magnet localization method 300 proceeds to step 368, where it is determined whether the cost function solution of step 362 is a solution for a first timepoint in the device magnetic data.

If the answer to step 368 is negative, then the magnet localization method 300 proceeds to step 370, whereby the minimization algorithm iterates based upon at least one parameter of the simulated positional information associated with the previous timepoint in the device magnetic data, in order to solve the cost function. Iterating may include iterating at least one, or all, of an x-position, a y-position, a z-position, a roll value, a pitch value, or a yaw value of the simulated positional information of the previous timepoint (e.g., the final or best estimate of any of the foregoing parameters from the previous timepoint). This improves processing speed, as well as the likelihood that the numerical method used will converge to a relevant solution.

Alternatively, if the answer to step 368 is affirmative, then the magnet localization method 300 proceeds to step 372, whereby the minimization algorithm iterates based upon nominal positional information in order to minimize the cost function. The nominal positional information may be, for example, arbitrary or random positional information, a best estimate, or based upon simulated positional information for the same timepoint for another magnet. Iterating may include iterating at least one, or all, of an x-position, a y-position, a z-position, a roll value, a pitch value, or a yaw value of the simulated positional information.

Following the execution of steps 366, 370, or 372, the method determinates at step 374 whether the computed value of the cost function meets termination criteria for terminating the magnet localization method 300. The termination criteria may include a threshold for the cost function solution. For example, when the minimization algorithm comprises a least squares analysis, the termination criteria may include an absolute threshold for a summation of squares and/or a relative threshold such as whether the sum of the current iteration is less than one or more previous sums. When the cost function surpasses the threshold (e.g., is lower than the threshold), the termination criteria are met.

If the answer to step 374 is affirmative, i.e., the termination criteria are met, then the simulated positional information of the simulated magnet at the most recent iteration of the minimization algorithm is assumed to be a sufficiently close estimation of the positional information of the real world magnet at the particular timepoint for which the cost function was minimized. Thus, the magnet localization method 300 has completed estimating the positional information for the magnet at that timepoint and terminates at termination 376 with respect to that timepoint.

Alternatively, if the answer to step 374 is negative, i.e., the termination criteria are not met, then the magnet localization method 300 returns to step 358 and repeats the process by iterating the simulated positional information until the termination criteria are met for that timepoint.

The foregoing steps are generally described for a single timepoint of the device magnetic data and for a single magnet. In multi-magnet systems, the magnet localization method 300 may execute the foregoing process contemporaneously for all magnets for a given timepoint, and then execute again for all remaining timepoints of the device magnetic data until the positional information of all magnets of the system is determined for all timepoints.

To aid understanding, a representative example of the foregoing method will be described for the magnet 132 in the tissue analysis apparatus 102, with reference to FIG. 1C. Before the cartridge 104 containing the magnet 132 is positioned adjacent to the magnetometer board 106, local magnetic field data is recorded by the magnetometer array 118a, i.e., each of the magnetic sensing elements of magnetometers 136a-136c (step 350). The cartridge 104 is then positioned adjacent to the magnetometer board 106 such that the magnet 132 is at a starting location or position adjacent to the magnetometer array 118a (step 352).

Thereafter, the magnet 132 is moved from its starting position by the contracting tissue construct 142 to a first position at a first timepoint. In this first position, the magnet 132 is characterized by positional information including its x-position, y-position, z-position, roll, pitch, and yaw ($x_0$, $y_0$, $z_0$, $roll_0$, $\theta_0$, $\phi_0$).

When the magnet is moved away from its starting position, each magnetic sensing element of each of the magnetometers 136a-136c changes its properties in response to the changing magnetic field of the magnet 132. Therefore, when the magnet 132 is in the first position at the first timepoint, the magnetometers 136a-136c output corresponding signals which are then processed and recorded as device magnetic data of the magnet 132 (particularly, components of the magnetic field) at locations corresponding to each of the magnetic sensing elements (step 354). Optionally, the local magnetic field data is subtracted from the device magnetic data (step 356).

A simulated magnet is simulated, e.g., by assuming a model for magnetic behavior (e.g., a dipole model) and positional information of the simulated magnet in theoretical space (step 358). The simulated positional information is characterized by variables including an x-position, y-position, z-position, roll, pitch, and/or yaw of the simulated magnet ($x_s$, $y_s$, $z_s$, $roll_s$, $\theta_s$, $\phi_s$). Simulated magnetic field data of the simulated magnet for the first timepoint is then computed at positions in theoretical space matching positions of each of the magnetic sensing elements of the magnetometer array 118a (step 360), based on the iteration steps 366-370.

A cost function is then computed by comparing the device magnetic data at the first timepoint with the simulated magnetic field data for the first timepoint (step 362). Because the result of the cost function is the first iteration and for the first timepoint in the series, the cost function iterates based on nominal positional information, e.g., nominal values for the simulated positional information ($x_s$, $y_s$, $z_s$, $roll_s$, $\theta_s$, $\phi_s$). The nominal values may be a best estimate (step 372). If the comparison between the device magnet and simulated magnetic field data based on the nominal positional information satisfies the termination criteria, then the nominal positional information is assumed to be a sufficiently close estimation of the positional information of the magnet 132 (step termination 376). However, if the comparison does not satisfy the termination criteria, then the foregoing process repeats at step 358. In particular, because the next iteration is no longer the first iteration for the first timepoint, the cost function iterates based on the previous iteration (step 366), i.e., iterates one or more simulated positional information values from those assumed in the previous iteration until the termination criteria are met (step 374).

Adapting the foregoing example to multi-magnet methods, steps 358-376 may be contemporaneously performed for each magnet. Further, for each magnet, the simulation steps 366-372 may iterate based on simulated positional information for one or more other magnets in the system (e.g., all other magnets). In this way, simulated positional information for each simulated magnet (and by extension the estimation of the positional information of each magnet) may account for the position of all magnets in the system. Further still, the estimation of the positional information of each magnet is based on simulated magnetic field data at numerous locations per magnet (i.e., locations corresponding to each magnetic sensing element of each magnetometer array). These advantages result in higher accuracy.

When processing large amounts of data, the foregoing multiparametric magnet localization method 300 can be time-intensive, in some cases, comprising the processing of several hundred parameters for tracking a plurality of magnets, e.g., across an array of tissues in a tissue analysis system. As a solution to this potential disadvantage, the magnet localization method 300 may include performing the foregoing steps 350-376 for a subset of the magnets of the system and/or a subset of timepoints in the device magnetic data, and then determining an empirical relationship between the estimated positional information of the subset of magnets and the device magnetic data recorded by the corresponding magnetometers, and optionally using the empirical relationship to estimate the positional information for subsequent timepoints without performing steps 350-376 for all timepoints. For example, the empirical relationship may include a polynomial function of the device magnetic data, which may be evaluated to estimate the positional information.

Another potential disadvantage of the foregoing magnet localization methods is the increase in positional noise resulting from the numerous magnetic sensing elements in the underlying system and the relatively close positioning of the magnets to the magnetic sensing elements. If $x_s$, $y_s$, or $z_s$ are sufficiently large when computing $\vec{B}_{model}$ for a particular magnet, noise on a given magnetic sensing element can translate to relatively large movements of that magnet, due to the relatively large gradient of the field-to-magnet position relationship at physical points distant to the magnet.

The estimated positional information produced by the magnet localization method 300 may be utilized for additional analysis. For example, the magnet localization method 300 may include comparing the estimated positional information of one or more magnets at different timepoints to determine positional changes of the magnet(s) over time, and optionally determining, based upon the determined positional changes, one or more properties of the tissue(s) operably attached to the magnet(s).

As previously stated, the foregoing methods account for different components of the magnetic field of each magnet at different locations, which more accurately reflects the actual properties of the magnetic fields being measured, rather than assuming all components are measured at a common location. Further, the robust methods described herein account for differences in the positions and movements of different magnets in multi-magnet systems. For example, the methods do not require that all magnets have the same starting position or even orientation relative to their corresponding magnetometer array. This reduces the time and criticality of experiment setup and calibration, which in turn increases throughput.

The method of FIG. 3 can be modified to employ various concepts of iterative modeling to provide yet further variations of the embodiments of the present disclosure. Thus, the specific order of steps shown in FIG. 3 is representative and should not be construed to limit the disclosure to the specific embodiments disclosed herein; rather, the magnet localization method of FIG. 3 shall be construed to include all possible embodiments along with the full scope of equivalents to which such steps or processes are entitled.

Figure 4:
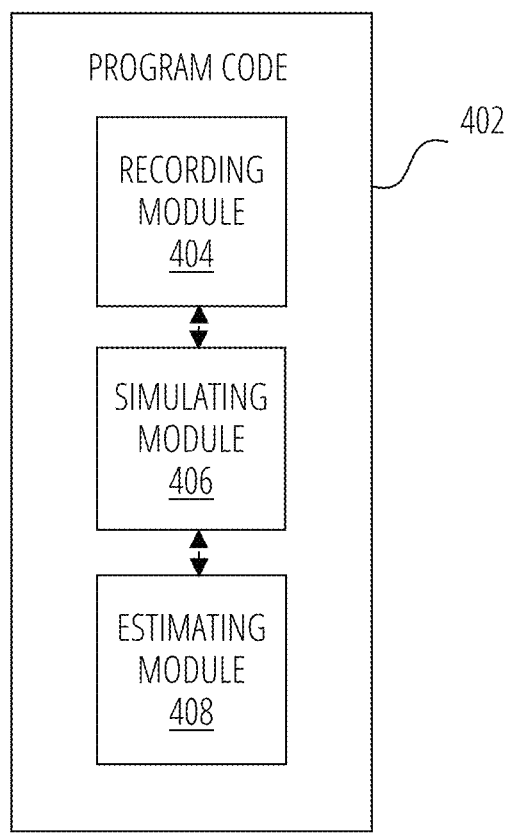
FIG. 4 is a diagram showing a structure of representative program code according to an embodiment of the present disclosure.

Any of the methods described herein may be implemented as computer-readable program code. Accordingly, FIG. 4 is a diagram showing a structure of representative program code 402 according to an embodiment of the present disclosure.

A recording module 404 may include computer-readable instructions relating to the recording of magnetic fields from one or more magnets of a system, e.g., the tissue analysis system. For example, recording module 404 may include instructions corresponding to steps 350, 354, and 356 as described with respect to FIG. 3, and may compute based upon on inputs received from magnetometers of the system. Outputs from the recording module 404 form inputs to a simulating module 406 and/or an estimating module 408.

The simulating module 406 may include computer-readable instructions relating to the simulating of a simulated magnet and magnetic fields thereof. For example, simulating module 406 may include instructions corresponding to steps 358 and 360 as described with respect to FIG. 3. Outputs from the simulating module 406 form inputs to the estimating module 408.

The estimating module 408 may include computer-readable instructions relating to the estimation of positional information of the one or more magnets of the system, which compute based upon inputs from the recording module 404 and simulating module 406. For example, the estimating module 408 may include computer readable instructions corresponding to steps 362 to 376 as described with respect to FIG. 3.

The foregoing program code structure is representative, and other embodiments may include additional or different modules implementing the methods described herein.

Figure 5:
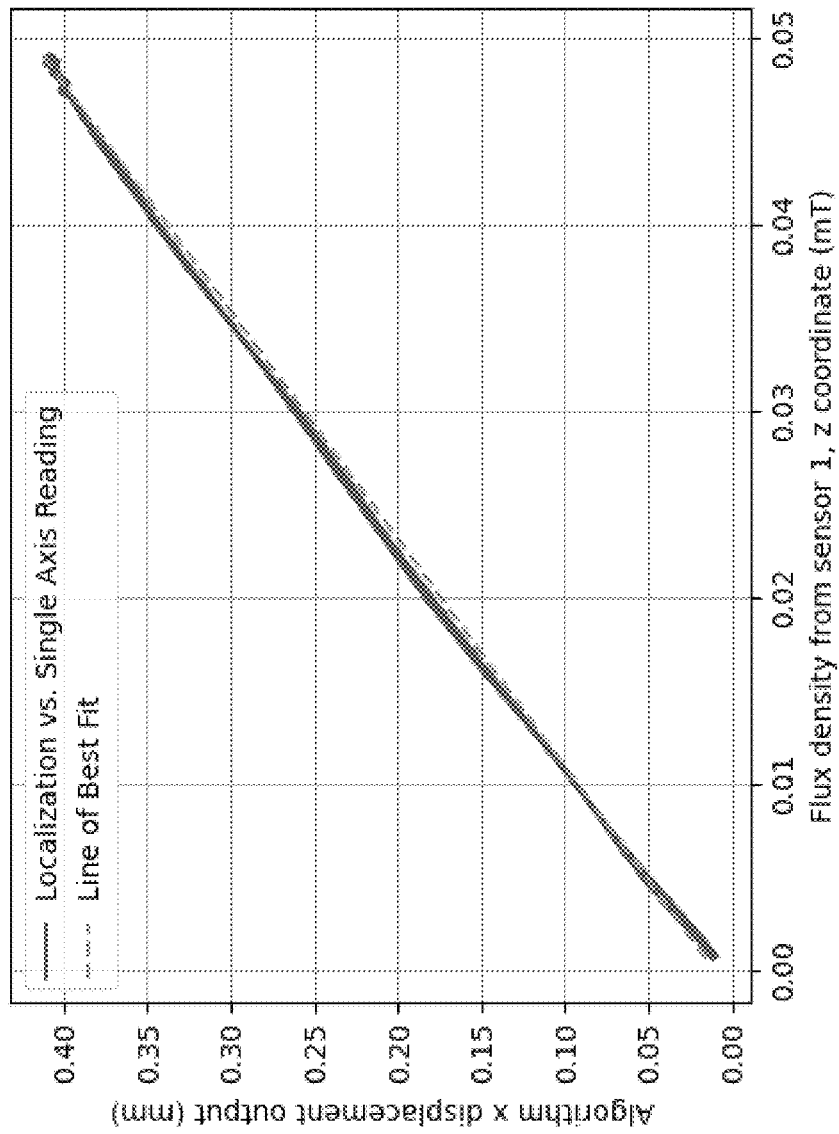
FIG. 5 is a plot of positional information of a magnet estimated by the magnet localization method of the present disclosure as a function of the measured flux density from a single axis of a single underlying magnetometer.

FIG. 5 shows a trace of the estimated positional information of a magnet as estimated by the magnet localization method of the present disclosure as a function of the measured z-coordinate flux density from a single axis of a single underlying magnetometer (solid line), and its corresponding line of best fit (dashed line). As shown, for a magnet of interest, the correlation between its estimated position and the recorded magnetic field may be highly linear. This evidences the accuracy of the magnet localization methods when each magnet of the system moves along a predictable trajectory, e.g., where its positional information changes one dimensionally in time due to its mechanical or structural constraints mandated by the system design. However, the foregoing method is not limited to such constrained circumstances.

FIG. 5 provides an example of an empirical relationship between the estimated positional information of a magnet and the device magnetic data recorded by the corresponding magnetometer. Based on such observation in FIG. 5, the output of a single axis of a single magnetometer can be multiplied by the slope of the line of best fit to determine positional change of the magnet. However, in some multi-magnet systems such as multi-well tissue analysis systems, this slope can vary between tissue-containing wells. The combinatorial approach of the magnet localization methods described herein can estimate these varying slopes, thereby allowing for far greater accuracy without sacrificing the processing speed to any appreciable degree.

The embodiments of the present disclosure are not limited to linear multiplication by a constant; rather, greater accuracy can be achieved by using a polynomial or other mathematical function with which such magnetic positional information can be more accurately correlated. However, in the interest of maintaining high linearity, the tissue analysis systems may position the magnet during measurement such that there is a high degree of linearity between its x-position change and its resulting change in magnetic field. For example, a magnet with a magnetic dipole moment vector pointing along the x-axis, placed in the midst of a cluster of magnetometers as described above may move within +/−3 mm in the x-direction and +/−1 mm in the y direction of the magnetic sensing element that detects the z-component of the magnetic field.

Figure 6:
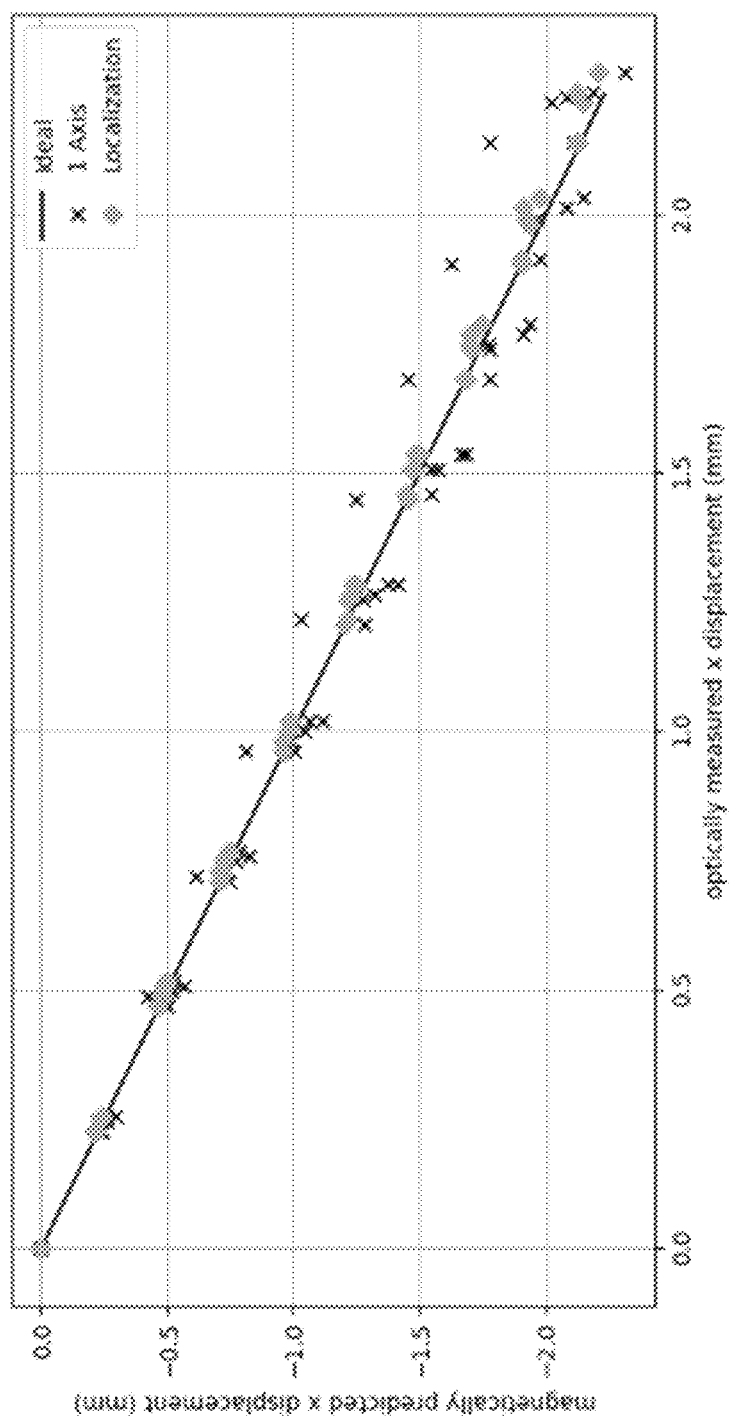
FIG. 6 is a plot of positional information of a magnet comparing optically tracked positional information with a) positional information estimated by the magnet localization method of the present disclosure and b) positional information estimated a single axis sensing method for a magnet displaced in discrete steps. Data represents a set of six magnets.

FIG. 6 is a plot of positional information of a magnet estimated by the magnet localization method of the present disclosure compared with and a single axis sensing method for a magnet displaced in discrete steps and optically tracked. Specifically, the plot tracks six different magnets as they are moved, and compares the optically measured position along the x-axis against a) the position along the x-axis as estimated by an embodiment of the magnet localization method described herein (indicated by diamonds) in which the estimated position is based on device magnetic data from nine magnetic sensing elements (three each within three magnetometers of a magnetometer array, yielding nine axes) and b) the position along the x-axis as estimated by a known method (indicated by x's) based upon a polynomial function of a single axis. The datapoints for each method are taken at the same timepoints.

As shown, the magnet localization method of the present disclosure tracks the ideal line with significantly less deviation than the single axis method, which indicates improved accuracy over known methods.

Figure 7:
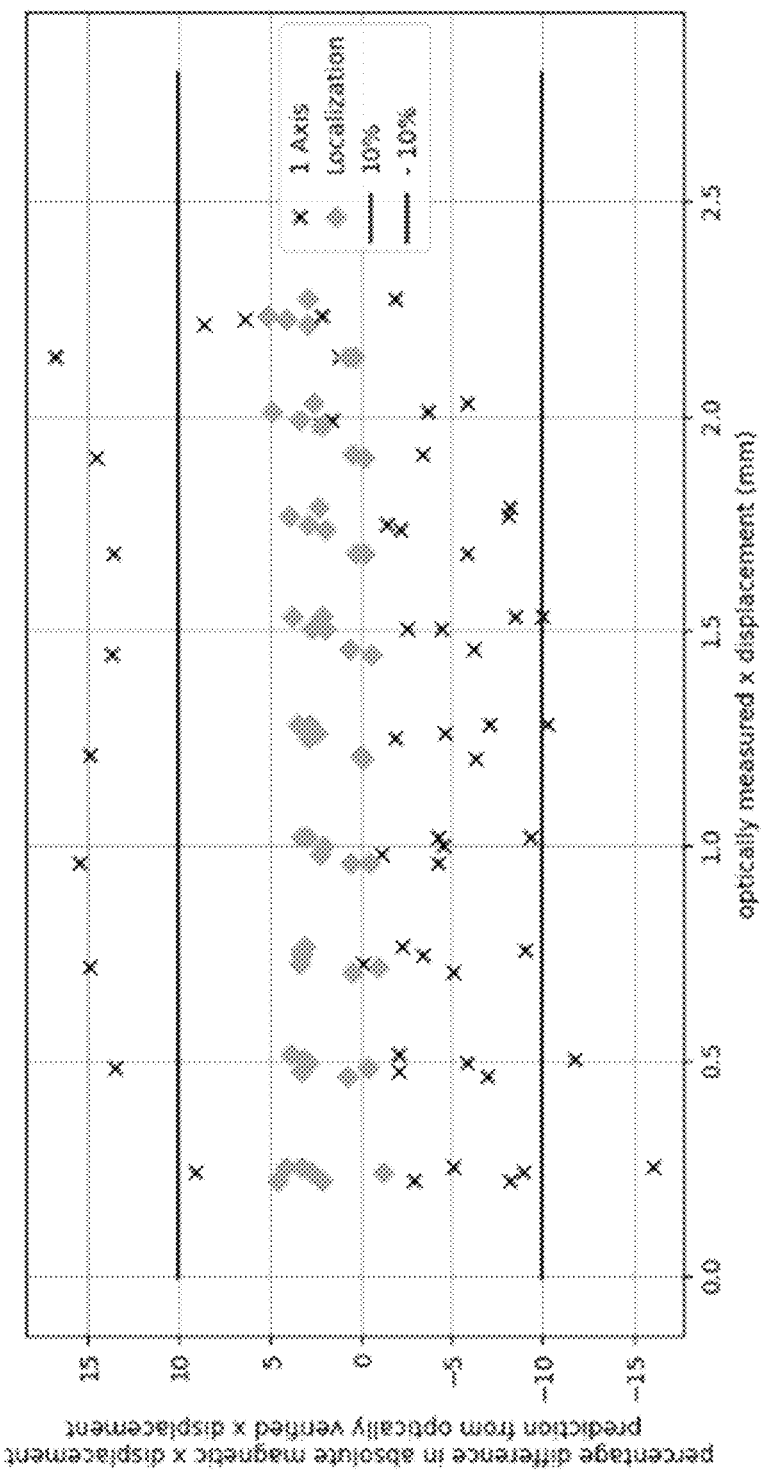
FIG. 7 is a plot comparing the accuracy of the two methods compared in FIG. 6.

FIG. 7 is a plot comparing the accuracy of the two methods plotted in FIG. 6. Specifically, the plot shows the percentage difference between the optically measured position along the x-axis and the estimated position using each of the two methods. As shown, the magnet localization method described herein (indicated by diamonds) has a percentage difference ranging from about negative one percent to about five percent, whereas the known method (indicated by x's) has significantly greater differences ranging between +/− fifteen percent. Accordingly, the methods described herein estimate positional information with greater accuracy and precision.

Figure 8:
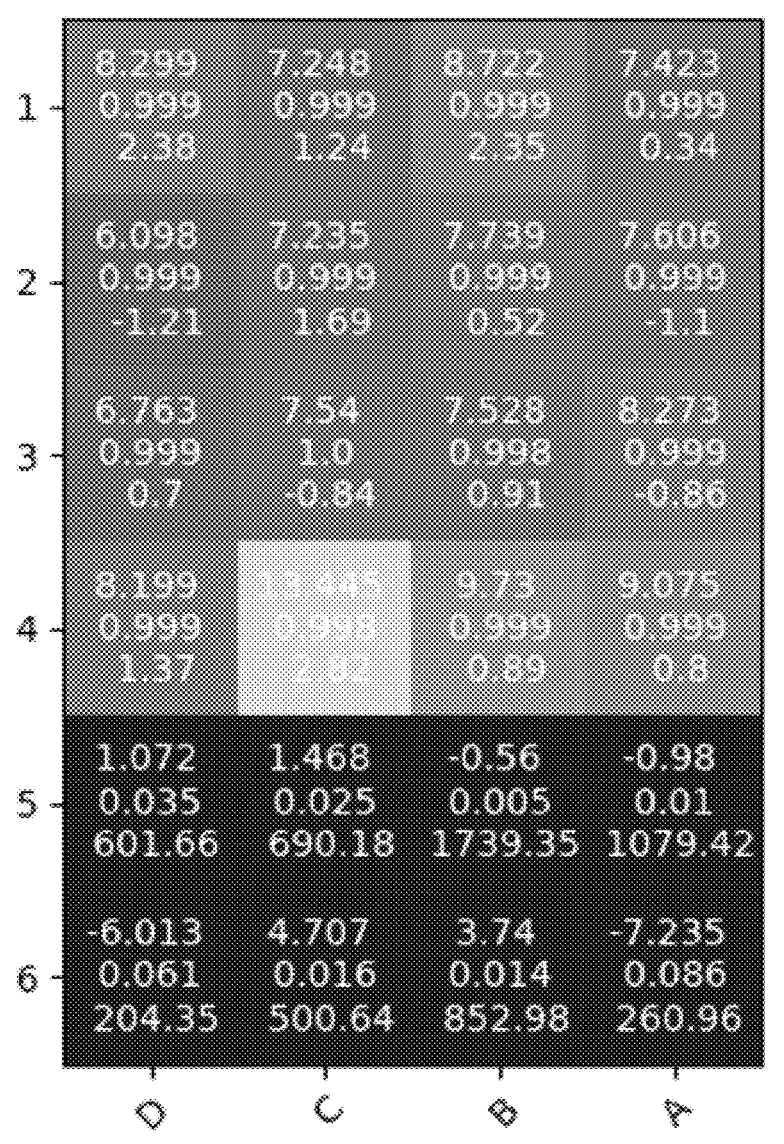

FIG. 8 shows the results from one magnet localization method of the present disclosure, wherein each square of the grid corresponds to a particular well within a twenty-four well microplate such as the microplate 122, wherein each well includes a magnet having a moving (contracting or beating) tissue construct operably connected thereto as described above with respect to FIG. 1A-FIG. 1G.

The squares represent a map of varying slopes (in the unit of mm/mT) across each magnet of the twenty-four tissues moving (or beating) within the plate. The upper number in each square represents an empirical relationship, i.e., a slope determined as described with respect to FIG. 5 by correlating estimated positional information of the magnet of a given well (as determined by the magnet localization method described herein) and the recorded magnetic field of one or more magnetometers of a magnetometer array disposed adjacent to that magnet. For each well, the slope can be multiplied by the magnetic fields recorded by the respective magnetometer at different timepoints to yield a positional change of the magnet.

The second row in each square shows the degree of fitness ($R^2$ coefficient) for each magnet. As shown, numerous wells have a very high degree of fitness greater than or equal to 0.998, including wells D1 through A4. Fit coefficients less than 0.95 (as shown in wells D5 through A6) may indicate that the magnet is not moving (beating) sufficiently to be of interest or relevant.

The third row shows the predicted percentage difference for a tissue contraction amplitude prediction. A smaller absolute value indicates higher accuracy. As shown, wells D1 through A4 all have absolute values less than or equal to 2.82. Again, wells D5 through A6 are not moving sufficiently to be of interest or relevant.

Figure 9:
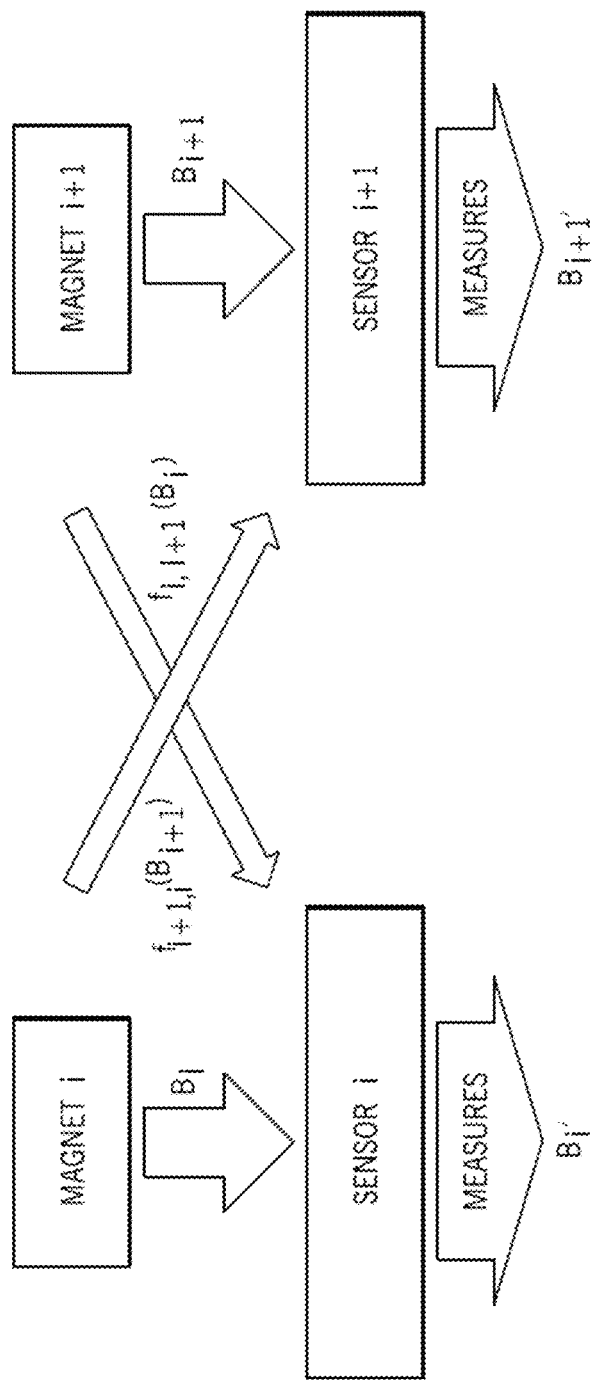
FIG. 9 illustrates inter-well "crosstalk" from single-axis measurements of a magnetometer.

This present disclosure further provides an approach that can resolve the "crosstalk" issue that adversely affects known methods and systems. As shown in FIG. 9, multiple tissue contractions in a tissue analysis system having a plurality of magnets, each operably connected to a tissue construct, particularly where the magnets are located close to each other and have temporally overlapping contractions, can add errors to the magnetic field data recorded by a particular magnetometer. This occurs because each magnetometer will measure the magnetic field changes caused by the magnet moving directly above it, as well as other nearby magnets.

Mathematically, due to the additive nature of magnetic fields, the magnetic field recorded by a particular magnetometer can be considered a superposition of the magnetic field from the magnet of the interest and crosstalk (or interfering) magnetic fields from the magnets adjacent to the magnet of interest. This relationship can be represented by the equation for a given sensor i, as follows:

$$B'_i = B_i + f_{i,i+1}(B_{i+1}) + f_{i,i+2}(B_{i+2}) + \ldots + f_{i,n}(B_n) \quad (5)$$

In equation (5), Bit is the magnetic field value measured at the magnetometer i, $B_i$ is the magnetic field generated by the magnet over the magnetic sensor i in absence of crosstalk, $f_{i,i+1}$ is the function relating the magnetic field of an adjacent magnet in absence of crosstalk, $B_{i+1}$ at its designated magnetic sensor i+1, and the interfering field it causes at the magnetic sensor i. Equations of this form can be prepared for each magnetometer and arranged into a system, which can be solved for individual fields ($B_i$, $B_{i+1}$, ..., $B_n$) in absence of crosstalk, as follows:

$$B'_1 = B_1 + f_{1,2}(B_2) + f_{1,3}(B_3)$$

$$B'_2 = B_2 + f_{2,1}(B_1) + f_{2,3}(B_3)$$

$$B'_3 = B_3 + f_{3,1}(B_1) + f_{3,2}(B_2) \quad (6)$$

In order to properly generate this system of equations, the function $f_{i,i+n}$ may be determined for the magnetometers surrounding the magnetometer of interest such that it can be determined how the magnetic field produced by a magnet moving directly over a given magnetometer affects the adjacent magnetometers.

$f_{i,i+n}$ represents the "slope" or other corresponding relationship between the estimated positional change of the magnet and the magnetic field recorded by the underlying magnetometers of the magnetometer array. It can be derived using the magnet localization method described herein to track the trajectory of each magnet independently, then simulating magnetic fields at adjacent sensors for each magnet in the absence of the others.

A solution of this system of equations 6 may be quickly determined and paired with the aforementioned single-sensor approach to greatly accelerate data analysis. In another embodiment, such slope or corresponding empirical relationship can be determined by controlling the motion of tissues, and thus that of the magnet, in time. The tissue constructs operably attached to the magnets are electrogenic, and thus, one tissue construct can be electrically stimulated to move (or contract) at a different time than the others, thereby allowing the determination of $f_{i,i+n}$ for the magnet attached to that particular tissue construct without interference from others.

The systems and devices described herein, particularly the tissue analysis systems, may include or form part of a computing device as described below having one or more processors and a non-transitory machine readable storage medium storing instructions, which when executed by the processor, executes the magnet localization methods and other methods described herein.

FIG. 10 is a block diagram illustrates components of a computing device 700. The reference numerals used to describe FIG. 10 do not necessarily correspond to other figures described herein.

The computing device 700 is configured to read instructions 724 from a non-transitory machine-readable storage medium (e.g., a hard drive storage system) and perform any one or more of the methodologies discussed herein, in whole or in part. Specifically, FIG. 10 shows the computing device 700 in the example form of a computer system within which the instructions 724 (e.g., software, a program, an application, an applet, an app, or other executable code) for causing the computing device 700 to perform any one or more of the methods discussed herein may be executed, in whole or in part. For example, the computing device 700 may be effective to execute all or a part of the method described above in reference to FIG. 3. Additionally, in some embodiments, the computing device may perform some or all functions of the tissue analysis systems described above with respect to FIG. 1A-FIG. 1F.

In some embodiments, the computing device 700 operates as a standalone device or may be connected (e.g., networked) to other computing devices. In a networked deployment, the computing device 700 may operate in the capacity of a server computing device or a client computing device in a server-client network environment, or as a peer computing device in a distributed (e.g., peer-to-peer) network environment. The computing device 700 may be implemented as any one or more of a number of electronic devices, and may include hardware, software, or combinations thereof, and may, as example, be a server computer, a client computer, a personal computer (PC), a tablet computer, a laptop computer, a netbook, a cellular telephone, a smartphone, a web appliance, a network router, a network switch, a network bridge, or any computing device capable of executing the instructions 724, sequentially or otherwise, that specify actions to be taken by that computing device. Further, while only a single computing device 700 is illustrated, the term "computing device" shall also be taken to include any collection of computing devices that individually or jointly execute the instructions 724 to perform all or part of any one or more of the methodologies discussed herein.

The computing device 700 includes a processor 702 (e.g., a central processing unit (CPU), a graphics processing unit (GPU), a digital signal processor (DSP), an application specific integrated circuit (ASIC), a radio-frequency integrated circuit (RFIC), or any suitable combination thereof), a main memory 704, and a static memory—706, which are configured to communicate with each other via a bus 708. The processor 702 may contain microcircuits that are configurable, temporarily or permanently, by some or all of the instructions 724 such that the processor 702 is configurable to perform any one or more of the methodologies described herein, in whole or in part. For example, a set of one or more microcircuits of the processor 702 may be configurable to execute one or more modules (e.g., software modules) described herein. The computing device 700 may further include a display component 710, such as one or more devices such light emitting diode (LED) display screens, liquid crystal display (LCD) screens, gas plasma-based flat panel displays, LCD projectors, or other types of display devices.

The computing device 700 may include one or more input devices 712 operable to receive inputs from a user. The input devices 712 can include, for example, a push button, touch pad, touch screen, wheel, joystick, keyboard, mouse, trackball, keypad, accelerometer, light gun, game controller, or any other such device or element whereby a user can provide inputs to the computing device 700. These input devices 712 may be physically incorporated into the computing device 700 or operably coupled to the computing device 700 via wired or wireless interface. For computing devices with touchscreen displays, the input devices 712 can include a touch sensor that operates in conjunction with the display component 710 to permit users to interact with the image displayed by the display component 710 using touch inputs (e.g., with a finger or stylus).

The computing device 700 may also include at least one communication interface 720, comprising one or more wireless components operable to communicate with one or more separate devices within a communication range of the particular wireless protocol. The wireless protocol can be any appropriate protocol used to enable devices to communicate wirelessly, such as Bluetooth, cellular (including 3GPP or ETSI standards), IEEE 802.11, or infrared communications protocols, such as an IrDA-compliant protocol. It should be understood that the communication interface 720 may also or alternatively comprise one or more wired communications interfaces for coupling and communicating with other devices.

The computing device 700 may also include a power supply 728, such as, for example, a rechargeable battery operable to be recharged through conventional plug-in approaches or through other approaches, such as capacitive charging. Alternatively, the power supply 728 may comprise a power supply unit which converts AC power from the power grid to regulated DC power for the internal components of the device 700.

The computing device 700 may also include a storage element 716. The storage element 716 includes the machine-readable medium on which are stored the instructions 724 (logic) embodying any one or more of the methodologies or functions described herein. The instructions 724 may also reside, completely or at least partially, within the main memory 704, within the processor 702 (e.g., within the processor's cache memory), or both, before or during execution thereof by the computing device 700. The instructions 724 may also reside in the static memory 706.

Accordingly, the memory 704 and the processor 702 may also be considered machine-readable media (e.g., tangible and non-transitory machine-readable media). The instructions 724 may be transmitted or received over a network 202 via the communication interface 720. For example, the communication interface 720 may communicate the instructions 724 using any one or more transfer protocols (e.g., HTTP).

In some embodiments, the computing device 700 is a distributed computing device, e.g., a cloud computing device distributed across a plurality of disparate servers. In some example embodiments, the computing device 700 may have one or more additional input components (e.g., sensors or gauges) (not shown). Embodiments of such input components include an electrical stimuli input (e.g., a stimulation lid or stimulation plate), an image input component (e.g., one or more cameras), an audio input component (e.g., a microphone), a direction input component (e.g., a compass), a location input component (e.g., a GPS receiver), an orientation component (e.g., a gyroscope), a motion detection component (e.g., one or more accelerometers), an altitude detection component (e.g., an altimeter), and a gas detection component (e.g., a gas sensor). Inputs harvested by any one or more of these input components may be accessible and available for use by any of the modules described herein.

As used herein, the term "memory" refers to a non-transitory machine-readable medium capable of storing data temporarily or permanently and may be taken to include, but not be limited to, random-access memory (RAM), read-only memory (ROM), buffer memory, flash memory, and cache memory. The machine-readable medium is non-transitory in that it does not embody a propagating signal. While the machine-readable medium is described in example embodiments as a single medium, the term "machine-readable medium" should be taken to include a single medium or multiple media (e.g., a centralized or distributed database, or associated caches and servers) able to store instructions 724. The term "machine-readable medium" shall also be taken to include any medium, or combination of multiple media, that is capable of storing the instructions 724 for execution by the computing device 700, such that the instructions 724, when executed by one or more processors of the computing device 700 (e.g., processor 702), cause the computing device 700 to perform any one or more of the methodologies described herein, in whole or in part. Accordingly, a "machine-readable medium" refers to a single storage apparatus or device as well as cloud-based storage systems or storage networks that include multiple storage apparatus or devices. The term "machine-readable medium" shall accordingly be taken to include, but not be limited to, one or more tangible (e.g., non-transitory) data repositories in the form of a solid-state memory, an optical medium, a magnetic medium, or any suitable combination thereof.

While the inventions have been described in terms of particular embodiments and illustrative figures, those of ordinary skill in the art will recognize that the inventions are not limited to the embodiments or figures described.

The detailed description set forth above in connection with the appended drawings, where like numerals reference like elements, are intended as a description of representative embodiments of the present disclosure and are not intended to represent the only embodiments. Each embodiment described m this disclosure is provided as an example or illustration and should not be construed as preferred or advantageous over other embodiments. The illustrative embodiments provided herein are not intended to be exhaustive or to limit the disclosure to the precise forms disclosed. Similarly, any steps described herein may be interchangeable with other steps, or combinations of steps, in order to achieve the same or substantially similar result. Further still, one or more features of any embodiment may be combined with one or more features of one or more embodiments to form additional embodiments, which are within the scope of the present disclosure.

Generally, the embodiments disclosed herein are non-limiting, and the inventors contemplate that other embodiments within the scope of this disclosure may include structures and functionalities from more than one specific embodiment shown in the FIGURES and described in the specification. It will be appreciated that variations and changes may be made by others, and equivalents employed, without departing from the spirit of the present disclosure. Accordingly, it is expressly intended that all such variations, changes, and equivalents fall within the spirit and scope of the present disclosure as claimed. For example, the present disclosure includes additional embodiments having combinations of any one or more features described above with respect to the representative embodiments.

In the foregoing description, specific details are set forth to provide a thorough understanding of representative embodiments of the present disclosure. It will be apparent to one skilled in the art, however, that the embodiments disclosed herein may be practiced without embodying all the specific details. In some instances, well-known process steps have not been described in detail in order not to unnecessarily obscure various aspects of the present disclosure.

The present application may include references to directions, such as "first," "second," "vertical," "horizontal," "front," "rear," "left," "right," "top," and "bottom," "below," "around," etc. These references, and other similar references in the present application, are intended to assist in helping describe and understand the particular embodiment (such as when the embodiment is positioned for use) and are not intended to limit the present disclosure to these directions or locations.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" means any number that is more than one, for example, two, three, four, five, etc. The term "about," "approximately," etc., means plus or minus 5% of the stated value. The term "based upon" means "based at least partially upon." The term "between" includes the values recited in connection therewith. The expressions "at least one of A, B, or C"; "at least one of A, B, and C"; and "at least one of A, B, and/or C" have the same meaning, i.e., any one of the following conditions satisfy all of the foregoing expressions: A; B; C; AB; AC; BC; ABC.

What is claimed is:

1. A magnet localization method, comprising:
   recording a magnetic field of each magnet of a plurality of magnets with a nearest magnetometer array of a plurality of magnetometer arrays, wherein the plurality of magnets are disposed within wells of a multi-well cartridge and each magnet is attached to a post of a plurality of posts, each post having a tissue of a plurality of tissues attached thereto, wherein the nearest magnetometer array for each magnet is a magnetometer array positioned adjacent to the well in which the magnet is disposed;
   simulating, at one or more locations of each of the magnetometer arrays, a simulated magnetic field including directional components of a simulated magnet, wherein the simulated magnet has simulated positional information in theoretical space;
   estimating positional information for each magnet based upon at least the recorded magnetic field of the magnet and iterating the simulated positional information of the simulated magnet; and
   tracking movement of each tissue based upon the estimated positional information of the magnet attached to the post to which the tissue is attached.

2. The magnet localization method of claim 1, further comprising causing movement of each tissue via at least one applied stimulus.

3. The magnet localization method of claim 1, wherein recording the magnetic field of each magnet comprises recording magnetic field data associated with different points in space.

4. The magnet localization method of claim 1, wherein estimating the positional information for each magnet is based upon the recorded magnetic field for the magnet.

5. The magnet localization method of claim 1, wherein estimating the positional information for each magnet comprises adjusting for crosstalk based upon the magnetic field of every other magnet of the plurality of magnets.

6. The magnet localization method of claim 1, wherein estimating the positional information for each magnet is based upon iterating the simulated positional information of all simulated magnets.

7. The magnet localization method of claim 1, wherein iterating the simulated positional information of the simulated magnet iterating at least one of an x-position, a y-position, a z-position, a roll value, a pitch value, or a yaw value of the simulated magnet.

8. The magnet localization method of claim 7, wherein iterating the simulated positional information of the simulated magnet comprises iterating each of the x-position, the y-position, the z-position, the roll value, the pitch value, and the yaw value of the simulated magnet.

9. The magnet localization method of claim 1, wherein estimating the positional information for each magnet is based upon a cost function of the magnetic field of the magnet and the simulated magnetic field of the simulated magnet in the well in which the magnet is disposed.

10. The magnet localization method of claim 9, wherein iterating the simulated positional information of the simulated magnet comprises determining whether a value of the cost function is from a first iteration of a cost minimization algorithm.

11. The magnet localization method of claim 1, wherein iterating the simulated positional information of the simulated magnet comprises iterating based upon simulated positional information from a previous iteration of a timepoint.

12. The magnet localization method of claim 1, wherein iterating the simulated positional information of the simulated magnet iterating based upon simulated positional information associated with a previous timepoint or based upon nominal positional information.

13. The magnet localization method of claim 9, wherein iterating the simulated positional information of the simulated magnet comprises determining whether a value of the cost function meets termination criteria.

14. The magnet localization method of claim 1, wherein each magnetometer of the plurality of magnetometers comprises a plurality of magnetic sensing elements, and wherein recording the magnetic field of each magnet of the plurality of magnets with the nearest magnetometer array of the plurality of magnetometer arrays comprises sensing a flux density of the magnet with the plurality of magnetic sensing elements in each magnetometer of the nearest magnetometer array.

15. The magnet localization method of claim 14, wherein recording the magnetic field of each magnet of the plurality of magnets with the nearest magnetometer array of the plurality of magnetometer arrays comprises sensing different axes of the magnetic field with different magnetic sensing elements.

16. The magnet localization method of claim 1, wherein for each magnet, estimating the positional information is based upon the simulated positional information of every simulated magnet.

17. A computer-implemented method for localizing magnets within a multi-well plate, the computer implemented method comprising:
- recording, by a processor, a magnetic field of each magnet of a plurality of magnets with a nearest magnetometer array of a plurality of magnetometer arrays, wherein each magnet is disposed within one well of a multi-well plate and is coupled to at least one post of a plurality of posts, each post having at least one tissue of a plurality of tissues attached thereto;
- simulating, by the processor, at one or more locations in each well of the multi-well plate, positional information in theoretical space of a simulated magnet;
- estimating, by the processor, positional information for each magnet based upon iterating the simulated positional information of the simulated magnet in the well in which the magnet is disposed; and
- tracking, by the processor, movement of each tissue based upon the estimated positional information for the magnet coupled to the post to which the tissue is attached.

18. A tissue analysis system, comprising:
- one or more processors; and a non-transitory machine readable storage medium storing instructions, which when executed by the one or more processors, causes the one or more processors to perform operations, including:
- recording a magnetic field of each magnet of a plurality of magnets with a nearest magnetometer array of a plurality of magnetometer arrays, wherein each magnet is coupled to a post of a plurality of posts in a different well of a multi-well plate, each post having a tissue of a plurality of tissues attached thereto;
- simulating at one or more locations in each well of the multi-well plate, at least one of a simulated magnetic field having directional components or a simulated positional information in theoretical space of a simulated magnet;
- estimating positional information for each magnet based upon the recorded magnetic field of the magnet and at least one of the simulated magnetic field or the simulated positional information of the simulated magnet in the well in which the magnet is disposed; and
- tracking movement of each tissue based upon the estimated positional information for the magnet coupled to the post to which the tissue is attached.

* * * * *